United States Patent
Rosenfeld et al.

(10) Patent No.: US 10,640,819 B2
(45) Date of Patent: May 5, 2020

(54) METHOD FOR DETECTING A GENETIC VARIANT

(71) Applicant: Cancer Research Technology Limited, London (GB)

(72) Inventors: Nitzan Rosenfeld, Cambridge (GB); Tim Forshew, London (GB); Francesco Marass, Cambridge (GB); Muhammed Murtaza, Phoenix, AZ (US)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 458 days.

(21) Appl. No.: 15/325,046

(22) PCT Filed: Jul. 17, 2015

(86) PCT No.: PCT/GB2015/052086
§ 371 (c)(1),
(2) Date: Jan. 9, 2017

(87) PCT Pub. No.: WO2016/009224
PCT Pub. Date: Jan. 21, 2016

(65) Prior Publication Data
US 2017/0204455 A1    Jul. 20, 2017

(30) Foreign Application Priority Data
Jul. 18, 2014   (GB) .................................. 1412834.2

(51) Int. Cl.
| | |
|---|---|
| *C12Q 1/6858* | (2018.01) |
| *G16B 20/00* | (2019.01) |
| *C12Q 1/6827* | (2018.01) |
| *C12Q 1/6883* | (2018.01) |
| *C12Q 1/6886* | (2018.01) |

(52) U.S. Cl.
CPC ......... *C12Q 1/6858* (2013.01); *C12Q 1/6827* (2013.01); *C12Q 1/6883* (2013.01); *C12Q 1/6886* (2013.01); *G16B 20/00* (2019.02); *C12Q 2527/146* (2013.01); *C12Q 2537/165* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2014/0088942 A1    3/2014  Li et al.

FOREIGN PATENT DOCUMENTS

WO    WO 2014/039556 A1    3/2014

OTHER PUBLICATIONS

Kim, Su Yeon et al., (2011) "Estimation of allele frequency and association mapping using next-generation sequencing data", BMC Bioinformatics, 12:.131.
Lynch, M. et al., (2009) "Estimation of allele frequency", Genetics, 182:295-301.
Turner, E. H. et al., (2009 ")Methods for genomic partitioning", Annu. Rev. Genomics Hum. Genet., 10:263-284.
Chenuil, A. et al., (2012) "How to infer reliable diploid genotypes from NGS or traditional sequence data: from basic probability to experimental optimization", Journal Evolutionary Biology, 25:949-960.
Lee, Joon et al., (2011) "On Optimal Pooling Designs to Identify Rare Variants Through Massive Resequencing", Genetic Epidemiology. 35(3):139-147.
Cao, C., et al., (2014) "Quantitative Group Testing-Based Overlapping Pool Sequencing to Identify Rare Variant Carriers", BMC Bioinformatics. Biomed Central, 15(1):195.

(Continued)

*Primary Examiner* — Joseph Woitach
(74) *Attorney, Agent, or Firm* — James S. Keddie; Bozicevic, Field & Francis LLP

(57) ABSTRACT

The present invention provides a method for detecting a genetic variant in a region of interest in a DNA sample comprising (i) determining, for a given sequencing platform, sequencing process and sequencing depth, the distribution of the number of reads supporting a genetic variant or plurality of genetic variants expected to be observed in the sequencing results of amplification reactions due to amplification and sequencing error (read count distribution); (ii) based on the read count distribution determined in step (i), establishing a threshold frequency at or above which the genetic variant must be observed in sequencing results of amplification reactions to assign a positive determination for the presence of the genetic variant in a given amplification reaction; (iii) partitioning the DNA sample into a plurality of replicate amplification reactions, so that the mean number of amplifiable template molecules of the region of interest in a replicate amplification reaction is fewer than the reciprocal of the threshold frequency determined in step (ii); (iv) performing the amplification reactions of step (iii) and sequencing the products of amplification reactions, (v) based on step (ii) and the results of step (iv), determining the presence/absence of the genetic variant in each replicate amplification reaction; and (vi) integrating the results of (v) to determine the presence/absence of the genetic variant in the region of interest in the DNA sample.

20 Claims, 12 Drawing Sheets

(56) References Cited

OTHER PUBLICATIONS

Cushing, A. et al., (2013) "RVD: a commandline program for ultrasensitive rare single nucleotide variant detection using targeted next-generation DNA resequencing", BMC Res. Notes, 6:.206.

Dering C. et al., (2011) "Comparison of collapsing methods for the statistical analysis of rare variants", BMC Proc., 5(9):1-4.

Macalalad, A. et al., (2012) "Highly Sensitive and Specific Detection of Rare Variants in Mixed Viral Populations from Massively Parallel Sequence Data", PLoS Comp. Biol., 8:10.

Flaherty et al., "Ultrasensitive detection of rare mutations using next-generation targeted resequencing", Nucleic Acids Research, 2012, 40(1): e2.

CDF_thresh=0.9999, compound calls using N≥2. Table 2:

| Sample number | Fraction of mutant DNA | Fraction of wild-type DNA | Expected number of mutant molecules | Reactions per sample (T) | T-choose -2 | Expected rate of FP | Approx. probability of a false negative | Expected TP | Expected FN | Observed FP | Observed TP | Observed FN |
|---|---|---|---|---|---|---|---|---|---|---|---|---|
| 1 | 0.03 | 0.97 | 28.8 | 48 | 1128 | 0.14977584 | 1.26E-11 | 10 | 1.26E-10 | 2 | 10 | 0 |
| 2 | 0.01 | 0.99 | 19.2 | 96 | 4560 | 0.6054768 | 1.13E-07 | 9.999999 | 1.13E-06 | 0 | 10 | 0 |
| 3 | 0.0033 | 0.9967 | 6.4 | 96 | 4560 | 0.6054768 | 0.01302792 | 9.869721 | 0.130279 | 3 | 10 | 0 |
| 4 | 0.0011 | 0.9989 | 6.4 | 288 | 41328 | 5.48753184 | 0.01302792 | 9.869721 | 0.130279 | 4 | 10 | 0 |
| 5 | 0.0004 | 0.9996 | 4.27 | 576 | 165600 | 21.988368 | 0.07621843 | 9.237816 | 0.762184 | 28 | 8 | 2 |
| | | | | Total | | 28.8366293 | | 48.97726 | 1.022744 | 36 | 48 | 2 |
| | | | | Average | | | 0.020454877 | | | | | |

*Approximate probability of a false negative - based on Poisson probability of <N copies, plus the probability that these would fall in fewer than N different reactions

FIG. 4A

CDF_thresh=0.9999, compound calls using N≥3. Table 3:

| Sample number | Fraction of mutant DNA | Fraction of wild-type DNA | Expected number of mutant molecules | Reactions per sample (T) | T-choose -3 | Expected rate of FP | Approx. probability of a false negative | Expected TP | Expected FN | Observed FP | Observed TP | Observed FN |
|---|---|---|---|---|---|---|---|---|---|---|---|---|
| 1 | 0.03 | 0.97 | 28.8 | 48 | 17296 | 0.00022966 | 1.68E-10 | 10 | 1.68E-09 | 0 | 10 | 0 |
| 2 | 0.01 | 0.99 | 19.2 | 96 | 142880 | 0.00189716 | 1.06E-06 | 9.999989 | 1.06E-05 | 0 | 10 | 0 |
| 3 | 0.0033 | 0.9967 | 6.4 | 96 | 142880 | 0.00189716 | 0.04781593 | 9.521841 | 0.478159 | 0 | 10 | 0 |
| 4 | 0.0011 | 0.9989 | 6.4 | 288 | 3939936 | 0.05231447 | 0.04781593 | 9.521841 | 0.478159 | 1 | 8 | 2 |
| 5 | 0.0004 | 0.9996 | 4.27 | 576 | 31684800 | 0.42071077 | 0.204236 | 7.95764 | 2.04236 | 1 | 7 | 3 |
| | | | | | Total | 0.47704922 | | 47.00131 | 2.998689 | | 45 | 5 |
| | | | | | Average | | 0.059973785 | | | | | |

*Approximate probability of a false negative - based on Poisson probability of <N copies, plus the probability that these would fall in fewer than N different reactions

FIG. 4B

|     | BC1     | BC2     | BC3     | BC4     | BC5     | BC6     | BC7     |
|-----|---------|---------|---------|---------|---------|---------|---------|
| BC1 | BC1/BC1 | BC1/BC2 | BC1/BC3 | BC1/BC4 | BC1/BC5 | BC1/BC6 | BC1/BC7 |
| BC2 | BC2/BC1 | BC2/BC2 | BC2/BC3 | BC2/BC4 | BC2/BC5 | BC2/BC6 | BC2/BC7 |
| BC3 | BC3/BC1 | BC3/BC2 | BC3/BC3 | BC3/BC4 | BC3/BC5 | BC3/BC6 | BC3/BC7 |
| BC4 | BC4/BC1 | BC4/BC2 | BC4/BC3 | BC4/BC4 | BC4/BC5 | BC4/BC6 | BC4/BC7 |
| BC5 | BC5/BC1 | BC5/BC2 | BC5/BC3 | BC5/BC4 | BC5/BC5 | BC5/BC6 | BC5/BC7 |
| BC6 | BC6/BC1 | BC6/BC2 | BC6/BC3 | BC6/BC4 | BC6/BC5 | BC6/BC6 | BC6/BC7 |
| BC7 | BC7/BC1 | BC7/BC2 | BC7/BC3 | BC7/BC4 | BC7/BC5 | BC7/BC6 | BC7/BC7 |

FIG. 7

METHOD FOR DETECTING A GENETIC VARIANT

FIELD OF THE INVENTION

The present invention relates to methods of detecting genetic variants in DNA samples.

BACKGROUND TO THE INVENTION

A genetic variant is one or more nucleotides which differ from a reference DNA sequence for a given region. For example, a genetic variant may comprise a deletion, substitution or insertion of one or more nucleotides.

A DNA sample may be analysed for known genetic variants or to discover previously unknown genetic variants in a region of interest by determining the DNA sequence in the region of interest and comparing the determined sequence to the reference sequence.

DNA sequencing can be performed using a variety of techniques, such as the classic chain termination method, or one of several high-throughput, next generation sequencing (NGS) methodologies, reviewed by Metzker, M. L., Nat Rev Genet 2010 January; 11(1): 31-46.

Illumina sequencing, 454 pyrosequencing, Heliscope single molecule sequencing, single molecule real time (SMRT) sequencing and Ion semiconductor sequencing platforms are examples of DNA sequencing methods based on the "sequencing by synthesis" principle. In these methods, the sequence of a template strand of DNA is determined through the detection of signals emitted as nucleotide bases are incorporated into a newly-synthesised complementary strand.

DNA sequencing platforms have error rates. For example, occasionally the polymerase used in the amplification reaction will incorporate the wrong nucleotide base in the complementary strand being synthesised, leading to an incorrect determination of the nucleotide at that position in the DNA template. The detection limit of NGS methods is defined by errors at two stages: library preparation (which usually involves amplification by PCR) and by sequencing itself.

This is problematic especially for the detection of genetic variants that will only be present in a DNA sample at low frequency, for example a frequency approaching or below the error rate of the sequencing method used. Under such circumstances, it is difficult or impossible to determine whether a genetic variant identified is real (i.e. actually present in the DNA template molecule) or an error.

For Illumina sequencing, the background error rate varies for different genetic variants and genomic locations and has a large variance. Therefore, detecting mutations which are present in a DNA sample at frequency of ~1% or lower is problematic.

Existing methods of DNA sequencing and genetic variant identification have limitations with regards to the detection of rare, novel variants in multiple regions, especially in samples having small amounts of DNA.

Methods are typically incapable of identifying mutations occurring at a frequency lower than or similar to the error rate of method used (i.e. background noise).

Digital PCR (dPCR; Vogelstein B., Kinzler K. W. Proc. Natl. Acad. Sci. U.S.A. 1999 96(16):9236-41; Sykes, P. J. et al., BioTechniques 1992 13(3): 444-9) is not useful for identification of novel (i.e. previously unidentified) genetic variants, as dPCR involves use of primers and assays designed to detect particular variants. Moreover, dPCR has a limited scope for analysing multiple regions of interest in parallel, especially where DNA sample is limited.

Other complex methods exist for tagging single DNA molecules from a single pool of DNA, such as Safe-SeqS and single-molecule molecular inversion probes (Kinde I, et al., Proc Natl Acad Sci USA. 2011 108(23): 9530-5; Hiatt J B, et al., Genome Res. 2013 23(5):843-54.).

These methods are not suitable for simultaneous analysis of multiple genes (i.e. multiple regions of interest) and when DNA is limited.

Several studies have demonstrated non-invasive detection of cancer DNA (Dawson S J, et al., N Engl J Med. 2013 368(13):1199-209; Forshew T, et al., Sci Transl Med. 2012 4(136):136ra68; Murtaza M, et al. Nature. 2013 497(7447): 108-12). However, major challenges persist in this field, such as (a) screening sufficient bases of the genome to detect relevant cancer mutations (b) screening of small quantities of fragmented DNA for such mutations, and (c) detection of low frequency mutant tumour DNA molecules amongst many 'wild-type' molecules.

For example, Forshew T, et al., Sci Transl Med. 2012 4(136):136ra68 describes screening of large regions of the genome for cancer mutations in blood, but the detection limit for this method was ~1%-2% allele frequency (AF).

SUMMARY OF THE INVENTION

The present invention provides a solution to the above problems.

Real genetic variants are identified by determining background frequencies for genetic variants at each position taking into account the error of the method (i.e. error rates of DNA amplification and sequencing platform).

In a first aspect, the present invention provides a method for detecting a genetic variant in a region of interest in a DNA sample comprising
 (i) determining, for a given sequencing platform, sequencing process and sequencing depth, the distribution of the number of reads supporting a genetic variant or plurality of variants expected to be observed in the sequencing results of amplification reactions due to amplification and sequencing error (read count distribution);
 (ii) based on read count distribution determined in step (i), establishing a threshold frequency at or above which the genetic variant must be observed in sequencing results of amplification reactions to assign a positive determination for the presence of the genetic variant in a given amplification reaction;
 (iii) partitioning the DNA sample into a plurality of replicate amplification reactions so that the mean number of amplifiable template molecules of the region of interest in a replicate amplification reaction is fewer than the reciprocal of the threshold frequency determined in step (ii);
 (iv) performing the amplification reactions of step (iii) and sequencing the products of amplification reactions,
 (v) based on step (ii) and the results of step (iv), determining the presence/absence of the genetic variant in each replicate amplification reaction; and
 (vi) integrating the results of (v) to determine the presence/absence of the genetic variant in the region of interest in the DNA sample.

The present invention provides a method for detecting a genetic variant in a region of interest in a DNA sample comprising (i) determining, for a given sequencing platform, the mean frequency and variance of the frequency at which a genetic variant or plurality of genetic variants is expected to be observed in the sequencing results of amplification reactions due to amplification and sequencing error;

(ii) based on the mean frequency and variance of the frequency determined in step (i), establishing a threshold frequency at or above which the genetic variant must be observed in sequencing results of amplification reactions to assign a positive determination for the presence of the genetic variant in a given amplification reaction;

(iii) partitioning the DNA sample into a plurality of replicate amplification reactions so that the mean number of amplifiable template molecules of the region of interest in a replicate amplification reaction is fewer than the reciprocal of the threshold frequency determined in step (ii);

(iv) performing the amplification reactions of step (iii) and sequencing the products of amplification reactions, (v) based on step (ii) and the results of step (iv), determining the presence/absence of the genetic variant in each replicate amplification reaction; and (vi) integrating the results of (v) to determine the presence/absence of the genetic variant in the region of interest in the DNA sample.

Advantageously, the method allows detection of genetic variants at very low frequency within a DNA sample. Accordingly, the method enables earlier identification (e.g. in the context of disease pathology such as cancer-related mutations) of the presence of genetic mutations (i.e. when the mutation is present at a lower frequency) in comparison with previously known methods for mutation detection. The method therefore finds use in a variety of applications, such as screening for tumour reappearance, tumour growth, development of drug resistance/tumour evolution and identification of therapeutically actionable mutations. The method also allows for the identification of the presence of genetic mutations at low frequencies with improved statistical confidence.

A key feature of the method of the invention is the partitioning of the DNA sample into a plurality of replicate amplification reactions (e.g. by dilution and aliquoting into wells) so that, on average, the number of amplifiable template molecules of the region of interest present in a replicate amplification reaction is fewer than the reciprocal of the threshold frequency for a positive determination. In this way, for each amplification reaction having an amplifiable template region in which the genetic variant is present, there is a high probability that the variant will be observed at a frequency greater than the threshold frequency for determining the presence of the variant. The method thereby allows detection of the presence of genetic variants in a DNA sample even when present at very low frequency within the DNA sample. For example, the method allows detection at a frequency of less than 1%.

Moreover, the present method is useful in discovery of genetic variants. That is, for a region of interest, the background levels for each of the three potential base changes from a reference DNA sequence can be readily determined, and frequencies for the genetic variant above background levels (in particular DNA samples) can subsequently be identified using the method. Thus, without screening for any particular genetic variant, new genetic variants at any position within the region of interest can be identified. This feature is associated with clear advantages in a wide range of fields, including diagnostics, prognostics, mutation discovery, monitoring of response to treatment and drug resistance.

In some embodiments, for the genetic variant to be determined as being present in the region of interest in the DNA sample in step (vi), a positive determination for the presence of the genetic variant must be made in more than one replicate amplification reaction in step (v). In some embodiments, a positive determination for the presence of the genetic variant must be made in at least 3 replicate amplification reactions.

In some embodiments, the genetic variant may be a single nucleotide variant, that is a change from one nucleotide to a different nucleotide in the same position. In some embodiments, the genetic variant may be an insertion or deletion, that adds or removes nucleotides. In some embodiments, the genetic variant may be a combination of multiple events including single nucleotide variants and insertions and/or deletions. In some embodiments, a genetic variant may be composed of multiple genetic variants present in different regions of interest.

Requiring a positive determination for the genetic variant in a plurality of replicate amplification reactions reduces the probability of a false positive determination of the genetic variant being present in the DNA sample. The method requiring multiple positive determinations in replicate amplification reactions therefore has higher specificity for the detection of genetic variants.

The mean frequency and coefficient of variation (CV) at which a given variant is observed (i.e. in sequencing results) as a result of error in the method used to sequence a DNA sample can be used to determine and/or model background levels (i.e. noise) for a genetic variant. These values can be used, for example, to determine cumulative distribution function (CDF) values and/or to calculate z-scores.

In turn, measurements and/or models of background noise for a genetic variant can then be used to establish threshold frequencies above which a genetic variant must be observed to be determined as being present in a given amplification reaction (a positive determination). For a positive determination, the frequency of the variant must be higher than the mean frequency at background levels.

In some embodiments of the method of the invention, the threshold frequency of step (ii) is determined using a binomial, over-dispersed binomial, Beta, Normal, Exponential or Gamma probability distribution model. In some embodiments, the threshold frequency at which a given genetic variant must be observed at or above to be determined as being present in a replicate amplification reaction is the frequency at which the cumulative distribution function (CDF) value of that genetic variant reaches a predefined threshold value (CDF_thresh) of 0.99, 0.995, 0.999, 0.9999, 0.99999 or greater.

In some embodiments of the method of the invention, the threshold frequency of step (ii) is determined using a z-score cut-off. Here, the background mean frequency and variance of the frequency for the genetic variant determined in step (i) are modelled with a Normal distribution, and the threshold frequency for calling a mutation is the frequency at the z-score which is a number of standard deviations above the background mean frequency. In some embodiments, the threshold frequency is the frequency at z-score of 20. In some embodiments, the threshold frequency is the frequency at z-score of 30.

In some embodiments, establishing a threshold frequency at or above which the genetic variant must be observed in sequencing results of amplification reactions to assign a positive determination for the presence of the genetic variant in a given amplification reaction comprises (a) based on the read count distribution determined for a plurality of genetic variants—which is optionally a normal distribution defined by the mean frequency and variance of the frequency determined for a plurality of genetic variants—in step (i), establishing a plurality of threshold frequencies at or above which the genetic variants should be observed in sequencing results of amplification reactions to assign a positive determination for the presence of the genetic variant in a given amplification reaction, and (b) based on step (a), establishing an overall threshold frequency at or above which a genetic variant must be observed in sequencing results of a given amplification reaction to assign a positive determination for the presence of the genetic variant in that amplification reaction, which is the threshold frequency at which 90%, 95%, 97.5%, 99% or more of the threshold frequencies determined in step (a) are less than this value.

In this way, threshold frequencies need not be determined for each possible base at each position of the region of interest, and an overall threshold based on a plurality of genetic variants can be used in the method of the invention.

In some embodiments, the mean number of amplifiable template molecules of the region of interest to be present in a given replicate amplification reaction is determined such that when the genetic variant is present in a single amplifiable template molecule of a replicate amplification reaction, the probability that a positive determination will be made for that replicate is 0.9 or greater.

This minimises the probability that a given replicate amplification reaction will incorrectly be determined as being negative for a genetic variant when the variant is in fact present.

In some embodiments, the plurality of reactions all have the same amount of starting template material from the sample. In some embodiments, different reactions have different amounts of template material from the sample. These amounts can be considered when estimating the allele frequency of genetic variants in the sample.

In some embodiments, step (i) comprises sequencing a DNA sample multiple times, to determine the read count distribution for a genetic variant or plurality of genetic variants, which is optionally a normal distribution defined by the mean frequency and variance of the frequency for a genetic variant or plurality of genetic variants.

Advantageously, when background error rates are empirically determined for genetic variants in a region of interest in this way, the estimate of the background error rate will be more accurate, thereby allowing greater sensitivity for detecting the presence of a genetic variant in the DNA sample, and with a greater degree of confidence.

In some embodiments, the read count distribution at which a genetic variant or plurality of genetic variants is expected to be observed in the sequencing results of amplification reactions due to amplification and sequencing error (optionally a normal distribution defined by the mean frequency and variance of the frequency at which a genetic variant or plurality of genetic variants is expected to be observed in the sequencing results of amplification reactions due to amplification and sequencing error) is determined in step (i) based on sequencer and/or polymerase error rates. In some embodiments, this is determined taking sequence context into account.

In some embodiments, step (i) comprises 'looking-up' a reference value or plurality of reference values in a database, chart, table, list, catalogue, index, directory, or register. In some embodiments the reference values are determined by sequencing a reference DNA sample multiple times, to determine the read count distribution for a genetic variant or plurality of genetic variants, which is optionally a Normal distribution defined by the mean frequency and variance of the frequency for a genetic variant or plurality of genetic variants. In some embodiments, the reference DNA sample is a 'matched normal' sample.

Advantageously, the method of the invention can be performed without having to determine background error rates empirically each time.

In some embodiments, following partitioning of the DNA sample in step (iii), each replicate amplification reaction has a mean of more than a single amplifiable template molecule for the region of interest per replicate amplification reaction. In some embodiments, the mean number of amplifiable template molecules per replicate amplification reaction will be more than 1 and less than 1000, more than 2 and less than 1000, or more than 5 and less than 1000.

Advantageously, the DNA sample need not be partitioned more than necessary to achieve the efficiencies of the method associated with partitioning of template molecules. This has advantages at least in terms of reducing running and materials costs.

In some embodiments, the method is capable of detecting genetic variants which are present within the population of amplifiable template molecules of a DNA sample at a frequency of less than 2%, less than 1%, less than 0.5%, less than 0.1% or less than 0.05%.

In some embodiments, partitioning the DNA sample into a plurality of replicate amplification reactions comprises diluting the DNA sample and aliquoting into replicate amplification reactions. For example, the amplification reactions may be carried out in separate wells. Alternatively, replicate amplification reactions can be partitioned by other means known to those skilled in the art.

In some embodiments of the method of the invention, replicate amplification reactions are performed in parallel, and sequencing of the products of amplification reactions is performed in parallel.

In some embodiments of the invention the method further comprises:
(vii) determining the frequency of the genetic variant in the DNA sample.

Advantageously, this allows determination of changes in the frequencies of genetic variants over time (e.g. over the course of disease and/or during the course of treatment) and/or differences in frequencies of genetic variants between samples.

Amplification reactions may be performed by one-step PCR or by two-step PCR.

In some embodiments, amplification reactions are performed using one or more primer pairs flanking the region of interest which integrate sample and/or amplification reaction replicate specific identifier sequences into the products of amplification. Identifier sequences may be defined as any series of DNA bases that is sufficiently different from another series of DNA bases such that when read along with an attached targeted region of interest, the identifier can be used to identify from which sample and/or amplification reaction replicate the targeted sequence originated. The terms "identifier sequences" and "barcodes" are used interchangeably herein.

In some embodiments, the primers integrate sequence adapters into the products of amplification. In some embodiments the primers flanking the region of interest comprise sample and/or amplification reaction replicate specific identifier sequences and sequence adapters allowing these identifier and adapter sequences to be added during a one-step PCR. In some embodiments universal "tagging" sequences are included within the primer pairs. A tagging sequence may be defined as any series of DNA bases that may be used as a target for subsequent rounds of PCR. Attachment of common tagging sequences to a plurality of primers will result, after amplification, in a plurality of products with these common tagging sequences attached. An optimal tagging sequence will be sufficiently different from the genome of interest to prevent non-specific amplification of the genomic sequence. In some embodiments the tagging sequence may comprise additional features such as a binding site for sequencing primers. In some embodiments a second round of PCR is performed, using primers that comprise the tagging sequences, sequence adapters and optionally additional barcodes, to attach sequencing adapters and optionally additional barcodes to the original PCR product. In some embodiments ligation is used to attach sequence adapters and optionally additional barcodes to the original PCR product. In some embodiments, a plurality of regions of interest are analysed in parallel.

In some cases the method may therefore be implemented as a high-throughput method, allowing screening of multiple regions of interest for genetic variants simultaneously. This has advantages in terms of the speed, efficiency and reducing running and materials costs.

In some embodiments of the method of the invention, the read count distribution may be defined as a normal distribution characterised by parameters which are the mean frequency and variance of the frequency at which a genetic variant or plurality of genetic variants is/are observed or expected to be observed in the sequencing results of amplification reactions due to amplification and sequencing error.

Read count distribution may be defined as the general set of probabilities to observe the non-reference allele at any count.

The read count distribution may be the distribution of the number of reads supporting a genetic variant or plurality of variants expected to be observed in the sequencing results of amplification reactions due to amplification and sequencing error. A read supporting a genetic variant is a positive read for a genetic variant.

For example, the read count distribution may be the general set of probabilities to observe the genetic variant or plurality of genetic variants, for a given sequencing platform, sequencing process and sequencing depth, due to amplification and sequencing error.

Read depth, also termed sequencing depth, may be defined as the number of times a specific genomic position (e.g. a given nucleotide) is read during the sequencing process.

The method of the invention finds use in a wide variety of applications. In fact, the method is useful for detection of genetic variants in any region of interest in any DNA sample, for any purpose.

In another aspect, the present invention provides the method as described hereinabove to detect and/or quantify tumour DNA in a sample. In some embodiments, the method is for detecting and/or quantifying circulating tumour DNA in a sample.

In some cases in accordance with any aspect of the present invention, the sample is a biological sample obtained from a subject. In some embodiments the sample is a tissue sample, for example a surgical sample. In some embodiments the sample is a liquid biopsy, such as blood, plasma, urine, seminal fluid, stool, sputum, pleural fluid, ascetic fluid, synovial fluid, cerebrospinal fluid, lymph, nipple fluid, or bronchial lavage. In some embodiments the sample is a cytological sample or smear or a fluid containing cellular material, such as cervical smear, nasal brushing, or esophageal sampling by a sponge (cytosponge), Endoscopic/gastroscopic/colonoscopic biopsy or brushing, cervical mucus or brushing.

Many of the above samples can be obtained non-invasively, and can therefore be taken regularly without great risk or discomfort to the subject.

Accordingly, in one aspect the present invention provides the method as described hereinabove in an in vitro method of diagnosis or prognosis or monitoring a disease.

The method can be used to analyse DNA samples for genetic variation associated with or predictive of susceptibility, resistance or response to a given therapy.

Accordingly, in another aspect the present invention provides a method of identifying a subject having an increased probability of developing a disease (i.e. having increased susceptibility to a disease), the method comprising: obtaining a DNA-containing sample from the subject, and carrying out the method in accordance with the first aspect of the invention on the DNA-containing sample obtained from the subject. In some cases, in accordance with this aspect of the invention, the DNA-containing sample is determined to comprise a disease-associated genetic variant, thereby identifying a subject as having an increased probability of developing a disease (as compared to a subject not having a disease-associated genetic variant detected in a DNA-containing sample).

In another aspect the present invention provides a method of diagnosis, the method comprising: obtaining a DNA-containing sample from a subject, and carrying out the method in accordance with the first aspect of the invention on the DNA-containing sample obtained from the subject. In some cases, in accordance with this aspect of the invention, the DNA-containing sample is determined to comprise a disease-associated genetic variant.

A subject or plurality of subjects who may have a particular susceptibility, resistance or response to a given therapy can be analysed for genetic variation predictive of such susceptibility, resistance or response. Accordingly, in one aspect the present invention provides the method as described hereinabove in a method of identifying genetic variation predictive of susceptibility, resistance or response to a therapy.

Accordingly, the present invention provides a method of selecting a patient for therapy, the method comprising: obtaining a DNA-containing sample from the patient, and carrying out the method in accordance with the first aspect of the invention on the DNA-containing sample obtained from the patient. In some cases, in accordance with this aspect of the invention, the DNA-containing sample is determined to comprise a disease-associated genetic variant (e.g. a risk allele) and/or a genetic variant predictive of resistance or response to a therapy. The method may further comprise selecting the patient for therapy based on the determination that the DNA-containing sample from the patient comprises a genetic variant. In some cases the method may further comprise a step of administering a therapy and/or recommending administration of a therapy based on the determination that the DNA-containing sample from the patient comprises a genetic variant.

The method of the invention can also be used to identify novel (i.e. previously unidentified) determinants and/or predictors of susceptibility to or prognosis of a disease, or of resistance or response to a therapy.

Accordingly, in another aspect the present invention provides a method of identifying a disease-associated genetic variant, the method comprising: obtaining a DNA-containing sample from a patient or plurality of patients having a disease, and carrying out the method in accordance with the first aspect of the invention on the DNA-containing sample obtained from the patient or plurality of patients. In some cases, in accordance with this aspect of the invention, the DNA-containing sample or samples is/are determined to comprise a genetic variant, which is thereby identified as being a disease-associated genetic variant. In accordance with this aspect, in some embodiments the patient or plurality of patients may have a particular clinical phenotype and/or disease prognosis.

Accordingly, in some embodiments the method identifies determinants or predictors of a particular clinical phenotype and/or disease prognosis.

In another aspect the present invention provides a method of identifying a genetic variant associated with resistance or response to a therapy, the method comprising: obtaining a DNA-containing sample from a patient or plurality of patients having resistance to or a response to a therapy for a disease, and carrying out the method in accordance with the first aspect of the invention on the DNA-containing sample obtained from the patient or plurality of patients. In some cases, in accordance with this aspect of the invention, the DNA-containing sample or samples is/are determined to comprise a genetic variant, which is thereby identified as being a genetic variant associated with resistance or response to a therapy.

In another aspect, the present invention provides methods for monitoring or evaluating response to a therapy, wherein the method in accordance with the first aspect of the invention is performed on DNA samples obtained from a patient at different stages of therapy (for example, pre-intervention and during/post intervention). Comparison of genetic variation in samples taken at different times may reveal changes in response to therapy. For example, genetic variation or the relative frequency of a genetic variant in samples obtained during or after therapy and absent from samples obtained before therapy may reflect e.g. tumour evolution and/or tumour burden, or other biologic responses to therapy.

In another aspect, the frequency of genetic variants, or the ratio of frequencies of different variants, can be used to predict, monitor, or evaluate response to therapy. In another aspect, the presence or the frequency of genetic variants, or the ratio of frequencies of different variants, can be used to predict the risk level or prognosis of a patient if the patient is not treated or if the patient is given one of a set of therapies.

BRIEF DESCRIPTION OF THE FIGURES

FIG. 4. Tables 2 and 3, showing results for proof of principle application of the method in a dilution series of cell lines.

FIG. 7. Representation of combination target specific primer barcodes. Each target specific primer was synthesised 7 times with 7 different barcodes. The forward and reverse primers were then combined to produce 49 different well barcode combinations by mixing together each of 7 forward primers with each of 7 reverse primers.

DETAILED DESCRIPTION OF THE INVENTION

Figure 1B:
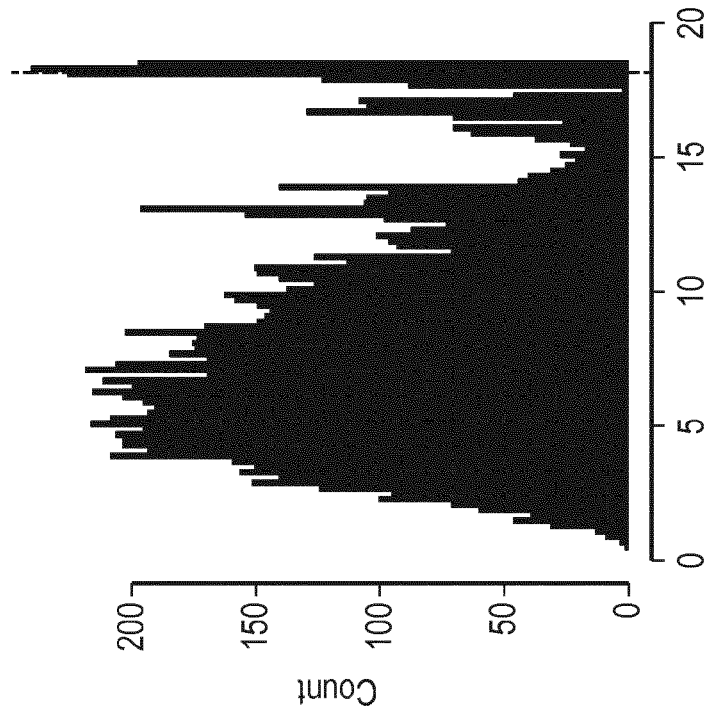
FIG. 1. Graphs showing Distributions of the background noise values of the amplicon sequencing process. (A) the mean, and (B) the coefficient of variation (CV, defined as standard deviation divided by the mean), for different single-nucleotide variants observed in an amplicon sequencing panel.

The method of the invention uses partitioning of the DNA sample into replicates within which a given variant if present will be at a frequency higher than in the total DNA sample, combined with detection of the mutation in multiple wells/reactions, thereby allowing a variant to be 'called' over error rates inherent in the method used for sequence determination; i.e. the sequencing platform.

Sequencer and polymerase error rates can be determined in various ways well known to those of skill in the art (Tindall, K. R., Kunkel, T. A. Biochemistry 1988 27(16): 6008-13; Forshew, T. et al. Sci. Transl. Med. 2012 4(136): 136ra68). Often these are published, and/or are available from manufacturers. The error rates can then be used to determine the expected frequency at which a genetic variant will be observed due to background noise.

Method error can also be introduced during e.g. library preparation, in the case of NGS methods.

Often, the error differs depending on the position of the base in the molecule being sequenced (see e.g. Loman N J et al., Nature Biotechnology 30: 434-439, 2012; Forshew, T. et al. Sci. Transl. Med. 2012 4(136):136ra68). One way to address this is by modelling the noise using parameters such as sequence context (Ross, M G et al., Genome Biology 2013 14:R51), however this is not able to give an accurate value for each possible change at each locus, and fails to account for changing properties of the sequencing system or amplification process over time.

Background frequencies for genetic variants at a particular base can also be determined empirically, by sequencing the region of interest for a reference DNA sample multiple times. For example, the reference DNA sample may be obtained from whole blood, or plasma from healthy subjects, or from a cell line. Results from sequencing the region of interest of the reference sample multiple times can then be used to establish background frequencies for each of four possible bases (A, G, T and C) at each position of the DNA sequence of the region of interest. This allows the frequency at which genetic variants are identified due to the error of the method (i.e. error rates of the DNA sequencing platform used) to be determined for each position of the DNA sequence of the region of interest. In some embodiments, the reference DNA sample may be a 'matched normal' sample. For example, the reference DNA sample may be obtained from the same tissue and/or sample type, from a healthy subject.

In some embodiments of the method of the invention, the mean and variance of the frequency of the genetic variant are determined for a specific panel of amplicons covering the region of interest.

'Region of interest' as used herein means the portion or portions of the genome being investigated. It may be a single sequence of DNA or a plurality of sequences of DNA. When the region of interest is a plurality of regions, these may be spread across the genome. That is, 'region of interest' encompasses a plurality of sequences of DNA being investigated being interspersed with portions of the genome which are not being investigated. In some cases the region of interest will depend on, for example, any clinical question being investigated.

For example, in some embodiments the region of interest may be a plurality of regions which are known to be or candidates for harbouring disease-associated genetic variants, or genetic variants influencing response to therapy. For example, in some embodiments the region of interest may be a panel of cancer-associated genes.

The frequency of a given nucleotide at a given position (allele frequency, AF) is determined as the proportion of reads for that position which identify that nucleotide at that position, out of the total number of determinations of the nucleotide at that position.

The AF for each nucleotide, at each position of the region of interest determined from each sequencing reaction of the reference sample can then be used to calculate the mean AF, and the coefficient of variation (CV) of the AF. The CV of the AF is calculated as the standard deviation of the AF divided by the mean AF.

The mean AF and CV of the AF can then be used to model background noise (i.e. sequencing error) for given genetic variant. For example, a Normal, Beta, Exponential or Gamma distribution or other function can be used to model the background noise for a genetic variant, depending on which model best fits the empirical distribution of the data. Similarly, the number of mutant reads and sequencing depths can be modelled with discrete functions.

Probability distributions and methods of modelling such to data are well known to those of skill in the art. Preferably several distributions will be modelled to AF data and the model with the best fit will be selected as the model for subsequent steps of the method of the invention. For example, different models may be analysed for Kolmogorov-Smirnov values for goodness of fit to the empirical data.

In the Examples below, Beta and Normal probability distributions are used.

Thresholds for Determining Presence of a Genetic Variant

Probability distributions fitted to the empirically determined background error AF and CV values, or based on predicted background error based on the sequencer and polymerase error rates, region of interest and genetic variant, can then be used to establish the threshold AF at or above which a genetic variant must be observed in the sequencing results of a replicate amplification reaction to be determined as being present in the DNA sample, herein referred to as the minimum detectable frequency (MDF).

For example, in Example 7 below the AF at z-scores of 20 and 30 were selected. That is, for a genetic variant to be determined as being present in the DNA sample in a given replicate amplification reaction, the frequency of that allele had to be 20 or more, or 30 or more standard deviations above the background mean AF for that particular variant.

Depending on the particular genetic variant in question, the region of interest, the sequencing platform used, etc., various z-score cut-offs are useful with the method of the invention. For example, the z-score threshold can be selected from one of 1, 2, 3, 4, 5, 6, 7, 8, 9, 10, 11, 12, 13, 14, 15, 16, 17, 19, 20, 22, 24, 26, 28, 30, 35, 40, 45, 50, 60, 70, 80, 90 and 100.

Using probability distributions, the cumulative probability of observing a particular genetic variant at a given AF, when the variant is actually present in a replicate amplification reaction, can be determined. This in turn can be used to establish a threshold frequency a genetic variant must be observed at or above in the products of a replicate amplification reaction to be determined as being present in the DNA sample.

The probability that putative mutations observed in sequencing data at a frequency at or above the MDF are 'real' rather than the result of sequencing error is very high. Such variants can therefore be determined as being present in a given amplification reaction with high confidence.

In some embodiments of the method of the invention, the threshold frequency of step (ii) is determined using a Beta probability distribution model of the background frequencies for genetic variants. Here, for each possible genetic variant at each position of the region of interest, the background mean frequency and variance of the frequency for the genetic variant determined in step (i) are used to define a Beta distribution. The threshold frequency at which a given genetic variant must be observed at or above to be determined as being present in a replicate amplification reaction is the frequency at which the cumulative distribution function (CDF) value of that genetic variant reaches a predefined threshold value (CDF_thresh). In some embodiments, CDF_thresh is 0.99, 0.995, 0.999, 0.9999, 0.99999 or greater.

For example, in Example 6 below, a cumulative probability (based on a Beta distribution) of observing a particular genetic variant a given AF of 0.9999 was used as the threshold AF for a positive determination (i.e. MDF). That is, the probability of observing a given genetic variant in sequencing results for a replicate amplification reaction, where the genetic variant is not present, is 0.01% or less. In some embodiments, the threshold frequency is the frequency at which the cumulative distribution function for the probability of observing the genetic variant at that frequency (CDF_thresh) is 0.8, 0.85, 0.9, 0.95, 0.96, 0.97, 0.98, 0.99, 0.995, 0.999, 0.9995, 0.9999, 0.99995 0.99999, 0.999995, 0.999999 or greater, corresponding to a probability of observing the genetic variant in sequencing results for an amplification reaction where the genetic variant is not present of 20%, 15%, 10%, 5%, 4%, 3%, 2%, 1%, 0.5%, 0.1%, 0.05% 0.01%, 0.005%, 0.001%, 0.0005%, 0.0001% or less.

In some embodiments, MDF values are determined for a plurality of possible genetic variants and subsequently used to establish an overall MDF for a given region of interest and/or panel of genetic variants of interest. Accordingly, in some embodiments, establishing a threshold frequency at or above which the genetic variant must be observed in sequencing results of amplification reactions to assign a positive determination for the presence of the genetic variant in a given amplification reaction comprises
(a) based on the mean frequency and variance of the frequency determined for the plurality of genetic variants in step (i), establishing a plurality of threshold frequencies at or above which the genetic variants should be observed in sequencing results of amplification reactions to assign a positive determination for the presence of the genetic variant in a given amplification reaction (that is, establishing MDFs for the plurality of genetic variants), and
(b) based on step (a), establishing an overall threshold frequency at or above which a genetic variant must be observed in the sequencing results of a given amplification reaction to assign a positive determination for the presence of the genetic variant in that amplification reaction (that is, establishing an overall MDF), which is the threshold frequency at which at least 90%, 95%, 97.5%, or 99% of the plurality of threshold frequencies determined in step (a) are less than this value.

In some embodiments, the overall MDF is the frequency at which 80%, 85%, 90%, 91%, 92%, 93%, 94%, 95%, 96%, 97%, 97.50%, 98%, 98.5%, 99%, or 99.5% or more of the MDF values determined for the plurality of genetic variants are smaller (i.e. less) than the overall MDF. In some embodiments the overall MDF is determined based on MDF values established for a plurality of genetic variants distributed across the region of interest. In some embodiments the plurality of genetic variants will be 5, 10, 20, 25, 30 or more variants.

The threshold for determining the presence of a genetic variant is selected—in conjunction with the number of copies of DNA template of the region of interest in a given replicate amplification reaction—to be such that if present, the frequency of the genetic variant in a given replicate amplification reaction is significantly higher than the background level for that genetic variation. In this way presence/absence of the genetic variant in a given amplification reaction can confidently be determined, minimising the possibility of a false positive determination.

Similarly, the threshold for determining the presence of a genetic variant is chosen such as to minimise the number of false negative determinations.

Numbers of Amplifiable Template Molecules Per Reaction

The lower limit at which a mutation can be identified is determined by the background frequency of a genetic variant (i.e. observed frequency due to method error). That is, for example, in a method whereby incorrect determinations are made at a frequency of 5%, real variants can only be distinguished from errors if their frequency is substantially greater than 5%.

The present method overcomes this problem by placing an upper limit on the mean number of amplifiable template molecules of the region of interest in a given replicate amplification reaction.

In the method of the present invention, the mean number of amplifiable template molecules of the region of interest (Mol_mean) in a given replicate amplification reaction is determined using the threshold for determining the presence of a genetic variant (MDF), as follows:

$$\text{Mol\_mean} < 1/\text{MDF}$$

Thus a genetic variant, if present in a given replicate amplification reaction, will be expected to be represented (as a fraction) within the mean total number of amplifiable template copies of the region of interest within that replicate amplification reaction at a frequency greater than the threshold frequency for determining the presence of the genetic variant in a given amplification reaction.

In this way, a single molecule having the variant will have a high probability of being detected at a frequency which is equal to or higher than the MDF determined in step (ii).

Here, the MDF can be the MDF calculated for a given genetic variant, or the overall MDF, which is an umbrella value representative of a plurality of MDFs, and which is described hereinabove.

For example, if a given genetic variant can only be confidently determined as being present in a DNA sample when observed at a frequency of, e.g. 5% or more (as defined by the MDF), the method requires that on average, fewer than 20 molecules be present in a given replicate amplification reaction. In this way, for any given replicate where the genetic variant is present (and up to 19 non-variant molecules are present), the variant will be observed at a frequency equal to or greater than 5%.

In the Examples provided below, the distribution of molecules into replicate amplification reactions is modelled with a Poisson distribution. The probability of positive determination for an amplifiable molecule having the genetic variant in a given amplification reaction can be determined based on a Poisson distribution. Alternatively, the distribution of molecules into replicate amplification reactions could be modelled with a Negative Binomial distribution.

Accordingly, in some embodiments, Mol_mean is determined using a Poisson distribution to model the number of amplifiable molecules that will be present in a given replicate amplification reaction and the expected mean number of amplifiable molecules. For different possible values of Mol_mean, the cumulative distribution function of the Poisson distribution is calculated. Mol_mean is then selected such that the cumulative distribution function value for the Poisson distribution will be greater than a threshold such as 0.8, 0.85, 0.9, 0.95 or 0.99.

In some embodiments of the method of the present invention the DNA sample is partitioned so that the mean number of amplifiable template molecules per reaction is such based on an expected Poisson distribution of molecules in reactions, a genetic variant if present will be detected more than 90% of the time. This threshold can be higher or lower, and plateaus as the mean number of molecules per reaction decreases to 1 (see e.g. FIG. 8). In some embodiments, the mean number of amplifiable template molecules per replicate amplification reaction is selected so that a genetic variant if present will be detected one of more than 80%, more than 81%, more than 82%, more than 83%, more than 84%, more than 85%, more than 86%, more than 87%, more than 88%, more than 89%, more than 90%, more than 91%, more than 92%, more than 93%, more than 94%, more than 95%, more than 96%, more than 97%, more than 98% and more than 99% of the time.

In the interests of efficiency and cost effective use of time and resources, it is preferred that a DNA sample is not partitioned more than necessary to achieve the efficiencies of the method associated with partitioning of template molecules. This has advantages at least in terms of reducing running and materials costs. Of course, the minimum number of molecules per amplification reaction will depend on the genetic variant to be determined, the region of interest, the error of the method (i.e. error rates of the DNA sequencing platform) and calculated thresholds etc. In certain embodiments of the method of the invention, it is preferred that more than one amplifiable template molecule of the region of interest is provided per replicate amplification reaction.

For example, in some embodiments the mean number of amplifiable template molecules per replicate amplification reaction will be more than 1 and fewer than Mol_mean.

In some embodiments, the mean number of amplifiable template molecules per replicate amplification reaction is more than 1 and less than 1000, more than 1 and less than 750, more than 1 and less than 500, more than 1 and less than 250, more than 1 and less than 200, more than 1 and less than 150, more than 1 and less than 100, more than 1 and less than 80, more than 1 and less than 60, more than 1 and less than 50, more than 1 and less than 40, more than 1 and less than 35, more than 1 and less than 30, more than 1 and less than 29, more than 1 and less than 28, more than 1 and less than 27, more than 1 and less than 26, more than 1 and less than 25, more than 1 and less than 24, more than 1 and less than 23, more than 1 and less than 22, more than 1 and less than 21, more than 1 and less than 20, more than 1 and less than 19, more than 1 and less than 18, more than 1 and less than 17, more than 1 and less than 16, more than 1 and less than 15, more than 1 and less than 14, more than 1 and less than 13, more than 1 and less than 12, more than 1 and less than 11, more than 1 and less than 10, more than 1 and less than 9, more than 1 and less than 8, more than 1 and less than 7, more than 1 and less than 6, more than 1 and less than 5, more than 1 and less than 4, more than 1 and less than 3, or more than 1 and less than 2.

In some embodiments, the mean number of amplifiable template molecules per replicate amplification reaction is more than 2 and less than 1000, more than 2 and less than 100, more than 2 and less than 75, more than 2 and less than 50, more than 2 and less than 40, more than 2 and less than 30, more than 2 and less than 29, more than 2 and less than 28, more than 2 and less than 27, more than 2 and less than 26, more than 2 and less than 25, more than 2 and less than 24, more than 2 and less than 23, more than 2 and less than 22, more than 2 and less than 21, more than 2 and less than 20, more than 2 and less than 19, more than 2 and less than 18, more than 2 and less than 17, more than 2 and less than 16, more than 2 and less than 15, more than 2 and less than 14, more than 2 and less than 13, more than 2 and less than 12, more than 2 and less than 11, more than 2 and less than 10, more than 2 and less than 9, more than 2 and less than 8, more than 2 and less than 7, more than 2 and less than 6, more than 2 and less than 5, more than 2 and less than 4, or more than 2 and less than 3.

In some embodiments, the mean number of amplifiable template molecules per replicate amplification reaction is more than 5 and less than 1000, more than 5 and less than 100, more than 5 and less than 75, more than 5 and less than 50, more than 5 and less than 40, more than 5 and less than 30, more than 5 and less than 29, more than 5 and less than 28, more than 5 and less than 27, more than 5 and less than 26, more than 5 and less than 25, more than 5 and less than 24, more than 5 and less than 23, more than 5 and less than 22, more than 5 and less than 21, more than 5 and less than 20, more than 5 and less than 19, more than 5 and less than 18, more than 5 and less than 17, more than 5 and less than 16, more than 5 and less than 15, more than 5 and less than 14, more than 5 and less than 13, more than 5 and less than 12, more than 5 and less than 11, more than 5 and less than 10, more than 5 and less than 9, more than 5 and less than 8, more than 5 and less than 7, or more than 5 and less than 6.

In some embodiments, the mean number of amplifiable template molecules per replicate amplification reaction is in the range of 2-40, 3-30, 4-30, 5-30, 5-25, 10-25, 15-25, or 18-22.

'Partitioning' may be achieved by any means suitable to separate replicate amplification reactions. For example, partitioning can be achieved by aliquoting the (diluted) DNA sample into separate wells. A variety of other methods for compartmentalising into separate (i.e. discrete, individual or independent) replicate amplification reactions will be known to the skilled person.

Requiring Plural Positive Replicates for a Positive Determination

To minimise the probability of a false positive determination of the presence of a genetic variant in a DNA sample, the method of the invention requires a genetic variant to be determined as being present in more than one replicate.

The mean number of molecules per reaction, and the number of replicate calls needed to minimised false positive calls, determine the number of reactions to be performed to obtain the required sensitivity.

The theoretical probability of a false positive occurring in N reactions out of total reactions T (P_fpNT) depends on the probability of a false positive in one reaction (P_fp1T, which is equal to 1−CDF_thresh) and the number of reactions, and is equal to $$P\_fpNT=((P\_fp1T)^N)*C\_NT=((1-CDF\_thresh)^N)*C\_NT$$

where C_NT is the combinatorial coefficient depending on the total number of reactions T, as follows ("!" indicates the factorial function)

$$C\_NT=T!/((T-N)!*N!)$$

The total number of false positives expected from this process is equal to the probability of false positives (P_fpNT), multiplied by the number of variants examined in this process. For example, when single-nucleotide variants are investigated, this will be the number of positions multiplied by 3 (for the three possible non-reference alterations).

Requiring a positive determination for the genetic variant in a plurality of replicate amplification reactions reduces the probability of a false positive determination of the genetic variant being present in the DNA sample. This is clear from the experimental examples below.

The method requiring multiple positive determinations in replicate amplification reactions therefore has higher specificity for the detection of genetic variants.

Figure 5:
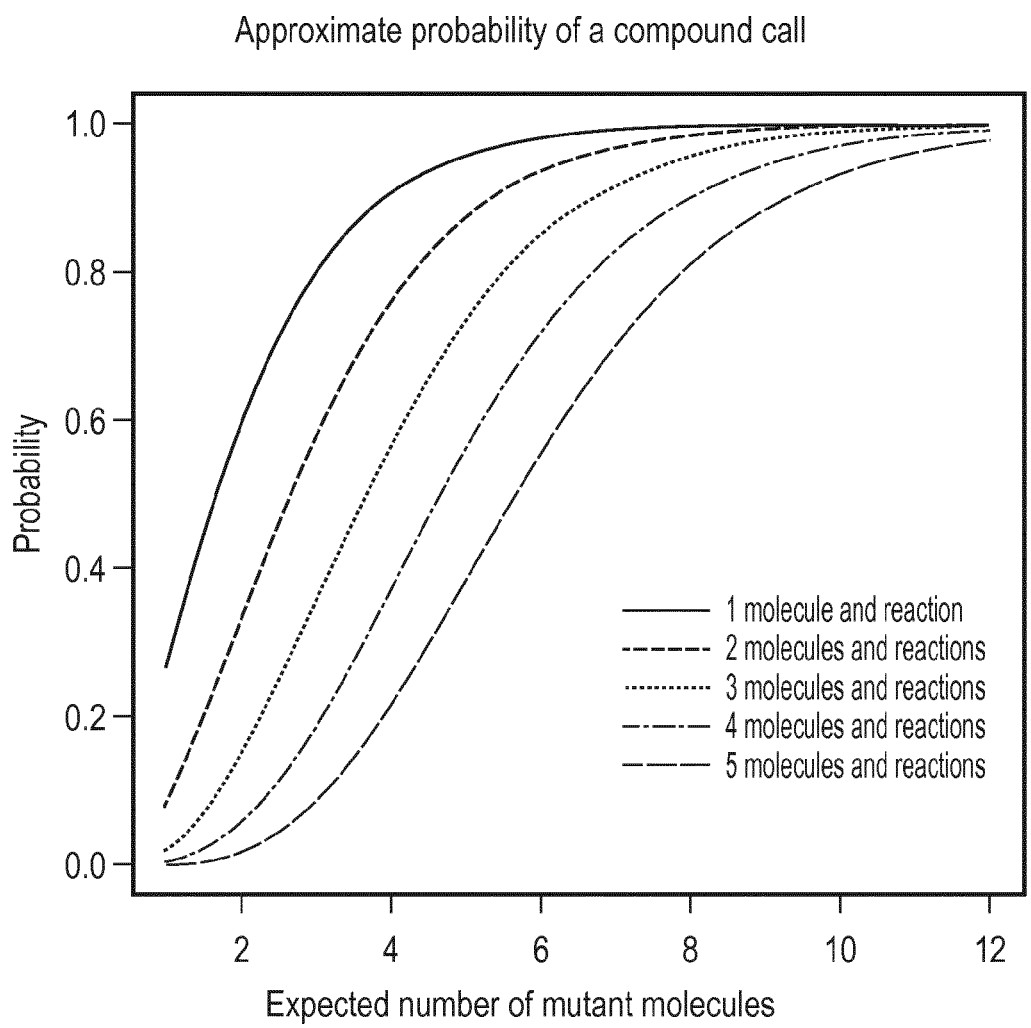
FIG. 5. Graph showing the probability of a compound mutation detection in multiple reactions, showing the Poisson probability to find at least N number of molecules in the sample as a function of the expected number of molecules (based on the concentration and starting amount of material), the different lines show a different N such that a compound call is made with ≥N positive reactions.

However, requiring a plurality of replicates to be positive for a given genetic variant also increases the probability that a false negative determination will be made. FIG. 5 shows the Poisson probability that at least N DNA template molecules will be present in the DNA sample as a function of the expected number of molecules (based on the concentration and starting amount of material).

The number of reactions, and the number of variant molecules in these reactions, should be high enough that, given the random distribution of mutant molecules, the probability that at least the required number of replicates contains one mutant is sufficiently high.

Therefore, the number of positive replicates required for a genetic variant to be determined as being present in a DNA sample in step (vi) will be chosen such as to minimise false positive and false negatives. That is, the number of positive replicates required will be determined to achieve a desired sensitivity and specificity of the method. In some embodiments, the number of positive replicates will be the number which maximises sensitivity and specificity of the method.

The number will always be greater than one. In some embodiments, the number will be 2, 3, 4, 5, 6, 7, 8, 9, or 10 replicates. In certain embodiments, the number will be 2 or 3.

The number may vary depending on the number and size of regions being analysed, the amount of DNA available, the total number of replicate amplification reactions etc.

The number may also vary based on the particular type of variation from the reference nucleotide; for example, whether the variant is a transition or transversion from the reference allele.

The number of positive replicates to be required can be determined in part by the total number of replicate amplification reactions for the DNA sample. For example, in some embodiments, for a genetic variant to be determined as being present in a DNA sample in step (vi), a positive determination for the presence of the variant must be made in more than 1%, 2%, 3%, 4%, 5%, 6%, 7%, 8%, 9% or 10% of replicates.

The optimal number of positive replicates to be required—that is to minimise false positives and false negatives—for a given variant and/or region of interest can be determined, for example, by performing the method of the invention on reference DNA samples.

The method of the invention requires integration of the results of presence/absence determinations for replicate amplification reactions for the ultimate determination of the presence/absence of the genetic variant in the region of interest in the DNA sample.

As used herein, 'integrating' means combining or consolidating the results of the presence/determinations for replicate amplification reactions.

Relationship Between the Variant Calling Threshold, Numbers of Amplifiable Template DNA Molecules and Number of Replicate Amplification Reactions As described above and in the experimental examples below, it will be immediately apparent to the skilled person that the threshold AF for determining the presence of a genetic variant in a replicate amplification reaction, the number of amplifiable template DNA molecules to be present in a given replicate amplification reaction and the number of replicates required to be 'positive' for a genetic variant to be determined as being present in a DNA sample are interrelated.

Essentially, the overriding principle is that the threshold for determining the presence of a genetic variant and the number of copies of DNA template of the region of interest should be selected such that if present, the frequency of the genetic variant in a given replicate amplification reaction is significantly higher than the background level for that genetic variation, and that the number of replicates to be positive should be selected to optimise sensitivity and specificity of the method.

In this way presence/absence of the genetic variant in a given amplification reaction can confidently be determined, minimising the possibility of a false positive determination.

The relative importance of sensitivity and specificity in establishing these parameters will also depend on the particular investigation. For example, in cases where the method of the invention is being used to identify novel mutations, the principal consideration may be sensitivity. Conversely, where a DNA sample is being analysed for a presence of a variant for informing therapeutic decisions the principal consideration may be specificity.

Tagged Amplicon Deep Sequencing

The method of the invention is suitable for use with high-throughput DNA sequencing methodologies. Advantageously, multiple regions of interest can be screened for mutations in parallel.

In the experimental examples below, the tagged amplicon deep sequencing (TAm-Seq) method is used. The method is described in detail in Forshew et al. 2012 Sci Transl Med 4(136) 136ra68. TAm-Seq allows amplification and deep sequencing of genomic regions spanning thousands of bases from as little as individual copies of fragmented DNA.

Figure 6:
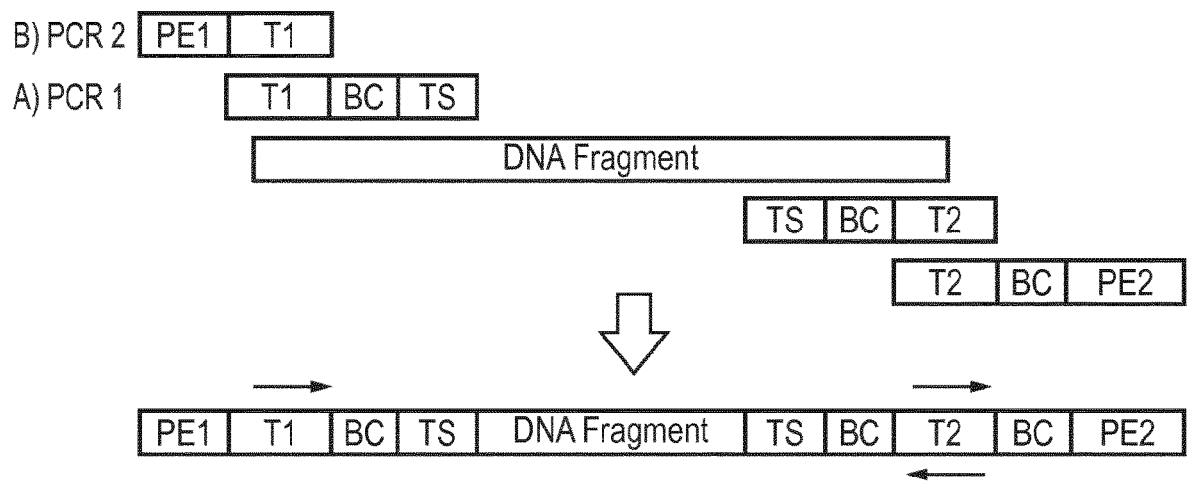
FIG. 6. Summary of an exemplary library preparation strategy. TAm-Seq primers are generated with multiple different barcodes. Each barcode combination is dispensed into a separate PCR well. A) The first PCR amplifies the region of interest, and adds molecular identifier tags (barcodes) that identify the reaction from the other replicate amplification reactions that have the same target-specific primers, but different barcodes. B) All PCR products from one sample are pooled and a second round of PCR attaches sequencer specific adapters and sample specific barcodes.

Briefly, primers are designed to generate amplicons that tile regions of interest in segments of a size range selected based on the quality (e.g. average fragment length) of the template DNA, incorporating universal sequencing adapter sequences and to tag each replicates with identifier sequences or 'barcode' (see FIGS. 6 and 7). The products are then sequenced and identifier sequences are used to demultiplex reads and align them to the genome.

Uses of the Method of the Invention

The method is useful for a wide range of applications, which will be immediately evident to the skilled person. Essentially, the method is useful for the detection of any genetic variant in any sample of interest.

For example, the method of the invention is useful in diagnostic and/or prognostic methods, or in microbe or virus analysis.

In particular, the method is useful for the detection of rare genetic variants and/or rare mutations. The method allows detection of variants present at a frequency of less than 1% in the DNA sample. Further, the method is suitable for detecting novel variants at such low frequency, as well as analysing samples for known variants.

Accordingly, the method enables earlier identification of the presence of genetic variants that may appear in the body such as in cancer or during pregnancy (i.e. when the genetic variant is present at a lower frequency).

In some cases in accordance with the method of any aspect of the present invention, the method comprises assaying a sample that has previously been obtained from a subject. The sample may in general be any suitable biological sample from which DNA can be isolated. In some cases, the sample is selected from the group consisting of: urine, saliva, blood, serum, faeces, other biological fluids, hair, cells and tissues.

In some embodiments in accordance with any aspect of the present invention, the DNA may be treated with bisulphite prior to performing the method. Bisulphite treatment of DNA converts unmethylated cytosine residues to uracil, but leaves methylated cytosine residues unaffected. In this way, the method is useful to detect variation in DNA methylation.

The ability of the method to detect the presence of variants at low frequency allows analysis of samples obtained by non-invasive and/or minimally invasive means. For example, liquid biopsies, such as blood, plasma, urine, seminal fluid, stool, sputum, pleural fluid, ascetic fluid, synovial fluid, cerebrospinal fluid or bronchial lavage samples. This has the advantage that samples can be taken regularly without great risk or discomfort to the subject. The sample may be fresh or have been previously stored (e.g. frozen), and/or may have been previously processed.

Moreover, the method is quantitative, allowing accurate measurement e.g. of circulating tumour DNA (ctDNA) mutant levels for clinical correlations or of other DNA, such as viral or microbial DNA.

Quantification can be performed, for example, by counting of the number of molecules determined as having the variant. This is suitable when the number of molecules having the variant is low. Quantification can also be performed by Poisson correction of the count, or by modelling the observed allele frequencies. Quantification can also be performed by taking into account the allele frequencies of the genetic variant in each of the plurality of reactions and the relative amounts of template in each reaction, for example by using an average or an average that is weighted by the amounts of material or by considering the fraction of reactions in which the variant was detected for different amounts of starting material.

For example, the method is useful for tumour load monitoring, wherein the method is used to monitor levels of ctDNA mutations, or to monitor reappearance of mutations, to inform as an early indicator of tumour regrowth. The method clearly has diagnostic and prognostic uses.

The method is also useful for monitoring drug resistance and/or tumour evolution in response to therapy. The method is particularly well suited for assessment of large numbers of regions of interest in parallel, and can be used to detect mutations in likely resistance pathways that might be early indicators of drug resistance. Such uses may be beyond of the capabilities of prior methods.

Furthermore, the method is useful in the primary diagnosis of tumours. The method can be used to look for ctDNA mutations in healthy patients for early diagnosis. For example, key oncogenes and tumour suppressor genes can be monitored.

The method is also useful with samples obtained from healthy subjects, for routine screening of or testing (i.e. monitoring) for genetic variants. In some embodiments the healthy subject may have recovered from a disease, for example the subject may be in remission from a cancer. Alternatively, the healthy subject may be at increased risk of a disease, for example the healthy subject may have a family history of a disease. The method of the invention can be used to routinely screen for genetic variants, optionally for genetic variants known to be associated with a given disease. In this way samples obtained from healthy subjects can be used to detect disease-associated genetic variants before clinical symptoms manifest, thereby facilitating early therapeutic intervention.

The method of the invention is useful for informing therapeutic decisions. That is, identification of genetic variants predictive of susceptibility, resistance or response to therapy can be used to select an appropriate course of treatment for a subject.

By way of example, the T790M mutation in EGFR is known to be associated with resistance to treatment of cancers using the EGFR inhibitors gefitinib and erlotinib. Subjects in which this mutation is identified using the method of the invention would therefore be identified as being unsuitable candidates for treatment using these inhibitors.

Similarly, the V600E mutation in B-Raf is associated with increased sensitivity to B-Raf inhibitors. Subjects in which this mutation is identified using the method of the invention would therefore be identified as good candidates for treatment using these inhibitors.

The method can be performed on DNA samples obtained from a subject at different time points, for example at different stages of a disease or course of treatment.

The method can be used to analyse DNA samples for genetic variation associated with or predictive of susceptibility, progression (i.e. prognosis), resistance or response to a given therapy. For example, the method can be used to identify novel (i.e. previously unidentified) determinants and/or predictors of susceptibility to or prognosis of a disease, or of resistance or response to a therapy.

Being quantitative, the method of the invention is useful for investigating the relative frequency of genetic variants at different stages of disease, in response to treatment and/or in healthy subjects over time.

This information can in turn can be used to inform therapeutic decisions. For example, an increase or decrease in the frequency of a genetic variant known/and or predicted to be associated with e.g. susceptibility or resistance to a particular therapy will guide the decision as to which therapy is most appropriate for the treatment of a given subject.

EXAMPLES

Example 1

Determination of Background Noise 41 amplicons were designed, covering all of TP53 and hotspot regions in EGFR, KRAS, BRAF and PIK3CA, and were read in forward and reverse directions, giving 82 read families in total (Table 1). The amplicons cover 5,038 bases including overlapping forward and reverse reads (excluding primer sequences).

TABLE 1

| Chromosome | Left coordinate | Right coordinate | Amplicon name |
| --- | --- | --- | --- |
| chr7 | 140453098 | 140453187 | BRAF_D0016_001_F |
| chr7 | 140453128 | 140453217 | BRAF_D0016_001_R |
| chr7 | 55241589 | 55241678 | EGFR_D0016_001_F |
| chr7 | 55241620 | 55241709 | EGFR_D0016_001_R |

TABLE 1-continued

| Chromosome | Left coordinate | Right coordinate | Amplicon name |
|---|---|---|---|
| chr7 | 55241658 | 55241745 | EGFR_D0016_002_F |
| chr7 | 55241659 | 55241746 | EGFR_D0016_002_R |
| chr7 | 55241705 | 55241792 | EGFR_D0016_003_F |
| chr7 | 55241706 | 55241793 | EGFR_D0016_003_R |
| chr7 | 55242385 | 55242474 | EGFR_D0016_004_F |
| chr7 | 55242397 | 55242486 | EGFR_D0016_004_R |
| chr7 | 55242427 | 55242516 | EGFR_D0016_005_F |
| chr7 | 55242448 | 55242537 | EGFR_D0016_005_R |
| chr7 | 55248931 | 55249020 | EGFR_D0016_006_F |
| chr7 | 55248938 | 55249027 | EGFR_D0016_006_R |
| chr7 | 55248989 | 55249078 | EGFR_D0016_007_F |
| chr7 | 55249011 | 55249100 | EGFR_D0016_007_R |
| chr7 | 55249062 | 55249151 | EGFR_D0016_008_F |
| chr7 | 55249101 | 55249190 | EGFR_D0016_008_R |
| chr7 | 55249144 | 55249233 | EGFR_D0016_009_F |
| chr7 | 55249160 | 55249249 | EGFR_D0016_009_R |
| chr7 | 55259388 | 55259477 | EGFR_D0016_010_F |
| chr7 | 55259409 | 55259498 | EGFR_D0016_010_R |
| chr7 | 55259456 | 55259545 | EGFR_D0016_011_F |
| chr7 | 55259485 | 55259574 | EGFR_D0016_011_R |
| chr7 | 55259526 | 55259615 | EGFR_D0016_012_F |
| chr7 | 55259546 | 55259635 | EGFR_D0016_012_R |
| chr12 | 25378518 | 25378607 | KRAS_D0016_001_F |
| chr12 | 25378524 | 25378613 | KRAS_D0016_001_R |
| chr12 | 25380216 | 25380305 | KRAS_D0016_002_F |
| chr12 | 25380248 | 25380337 | KRAS_D0016_002_R |
| chr12 | 25398246 | 25398335 | KRAS_D0016_003_F |
| chr12 | 25398248 | 25398337 | KRAS_D0016_003_R |
| chr3 | 178936028 | 178936117 | PIK3CA_D0016_001_F |
| chr3 | 178936046 | 178936135 | PIK3CA_D0016_001_R |
| chr3 | 178952022 | 178952111 | PIK3CA_D0016_002_F |
| chr3 | 178952056 | 178952145 | PIK3CA_D0016_002_R |
| chr17 | 7572903 | 7572992 | TP53_D0016_001_F |
| chr17 | 7572942 | 7573031 | TP53_D0016_001_R |
| chr17 | 7573904 | 7573993 | TP53_D0016_002_F |
| chr17 | 7573930 | 7574019 | TP53_D0016_002_R |
| chr17 | 7573975 | 7574064 | TP53_D0016_003_F |
| chr17 | 7573988 | 7574077 | TP53_D0016_003_R |
| chr17 | 7576789 | 7576878 | TP53_D0016_004_F |
| chr17 | 7576828 | 7576917 | TP53_D0016_004_R |
| chr17 | 7576873 | 7576960 | TP53_D0016_005_F |
| chr17 | 7576874 | 7576961 | TP53_D0016_005_R |
| chr17 | 7576996 | 7577085 | TP53_D0016_006_F |
| chr17 | 7577026 | 7577115 | TP53_D0016_006_R |
| chr17 | 7577074 | 7577163 | TP53_D0016_007_F |
| chr17 | 7577093 | 7577182 | TP53_D0016_007_R |
| chr17 | 7577434 | 7577523 | TP53_D0016_008_F |
| chr17 | 7577439 | 7577528 | TP53_D0016_008_R |
| chr17 | 7577484 | 7577573 | TP53_D0016_009_F |
| chr17 | 7577523 | 7577612 | TP53_D0016_009_R |
| chr17 | 7577561 | 7577650 | TP53_D0016_010_F |
| chr17 | 7577578 | 7577667 | TP53_D0016_010_R |
| chr17 | 7578120 | 7578209 | TP53_D0016_011_F |
| chr17 | 7578124 | 7578213 | TP53_D0016_011_R |
| chr17 | 7578173 | 7578262 | TP53_D0016_012_F |
| chr17 | 7578189 | 7578278 | TP53_D0016_012_R |
| chr17 | 7578228 | 7578316 | TP53_D0016_013_F |
| chr17 | 7578229 | 7578317 | TP53_D0016_013_R |
| chr17 | 7578343 | 7578432 | TP53_D0016_014_F |
| chr17 | 7578361 | 7578450 | TP53_D0016_014_R |
| chr17 | 7578407 | 7578496 | TP53_D0016_015_F |
| chr17 | 7578434 | 7578523 | TP53_D0016_015_R |
| chr17 | 7578483 | 7578572 | TP53_D0016_016_F |
| chr17 | 7578492 | 7578581 | TP53_D0016_016_R |
| chr17 | 7579284 | 7579373 | TP53_D0016_017_F |
| chr17 | 7579319 | 7579408 | TP53_D0016_017_R |
| chr17 | 7579364 | 7579452 | TP53_D0016_018_F |
| chr17 | 7579365 | 7579453 | TP53_D0016_018_R |
| chr17 | 7579405 | 7579494 | TP53_D0016_019_F |
| chr17 | 7579444 | 7579533 | TP53_D0016_019_R |
| chr17 | 7579488 | 7579577 | TP53_D0016_020_F |
| chr17 | 7579527 | 7579616 | TP53_D0016_020_R |
| chr17 | 7579677 | 7579765 | TP53_D0016_021_F |
| chr17 | 7579678 | 7579766 | TP53_D0016_021_R |
| chr17 | 7579816 | 7579905 | TP53_D0016_022_F |
| chr17 | 7579839 | 7579928 | TP53_D0016_022_R |
| chr17 | 7579887 | 7579976 | TP53_D0016_023_F |
| chr17 | 7579892 | 7579981 | TP53_D0016_023_R |

Each locus can change to one of three possible non-reference alleles. Excluding known polymorphisms, polymorphisms identified in the cell-lines used, and loci that cannot be modelled, a total of 13,278 possible single-base changes were considered.

Sequencing data for this panel of amplicons was collected from 336 replicate amplifications of LNCaP cell line (a human prostate adenocarcinoma, androgen-sensitive cell line; ATCC CRL-1740) DNA samples.

For each base change in each read family (amplicon and read direction), other than the loci excluded above, the mean allele frequency (AF) and the coefficient of variation (CV) of the AF were calculated. For a given allele (i.e. genetic variant), the AF calculated as the proportion of reads containing this allele out of all the reads in that read family.

Figure 1A:
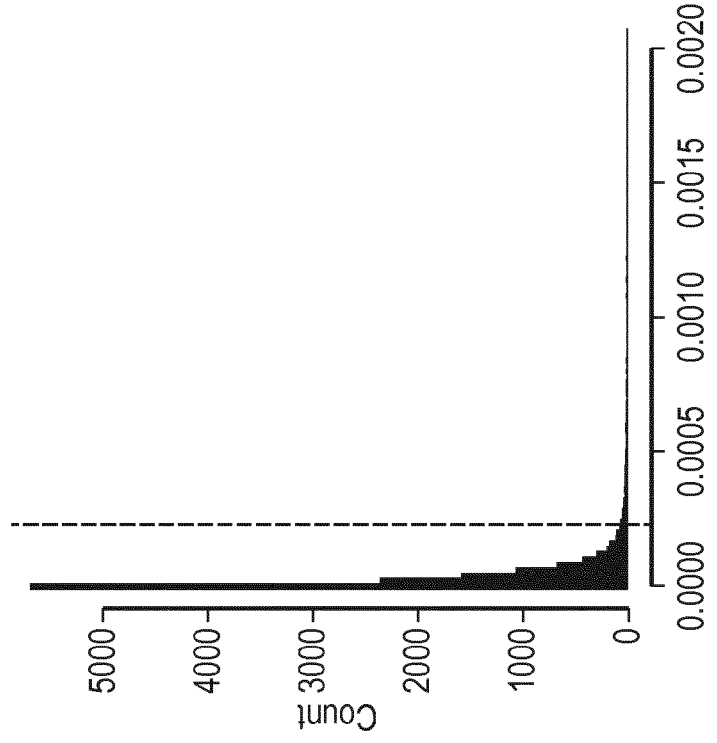
Figure 2A:
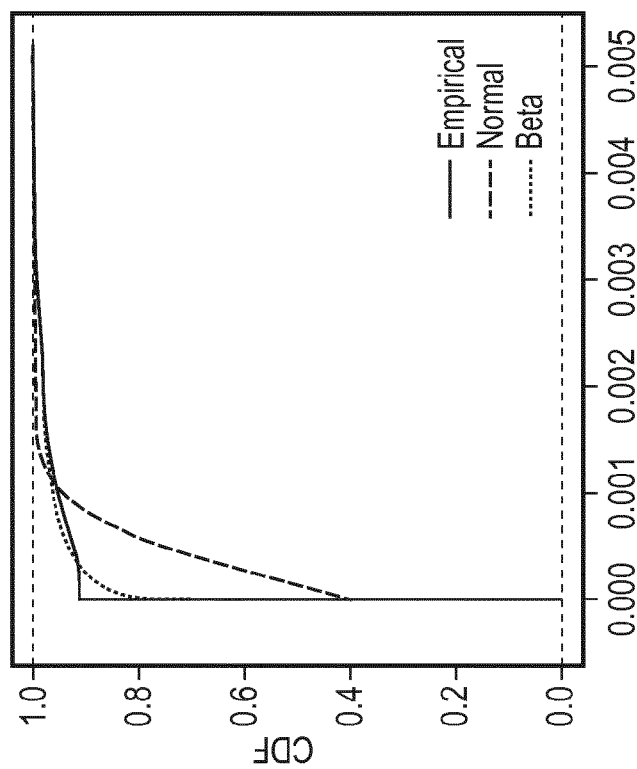
FIG. 2. Graphs showing the cumulative distributions for several base changes, and the cumulative distribution functions for the Normal distribution, and the Beta distribution, fitted using the values for the mean and CV that were calculated for those base changes, compared against the empirical distributions of the data. (A) EGFR_D0016_006_R 55248959 C>G. (B) EGFR_D0016_009_F 55249159 G>T. (C) EGFR_D0016_003_R 55241757 C>A. (D) EGFR_D0016_012_R 55259573 G>C.
Figure 2B:
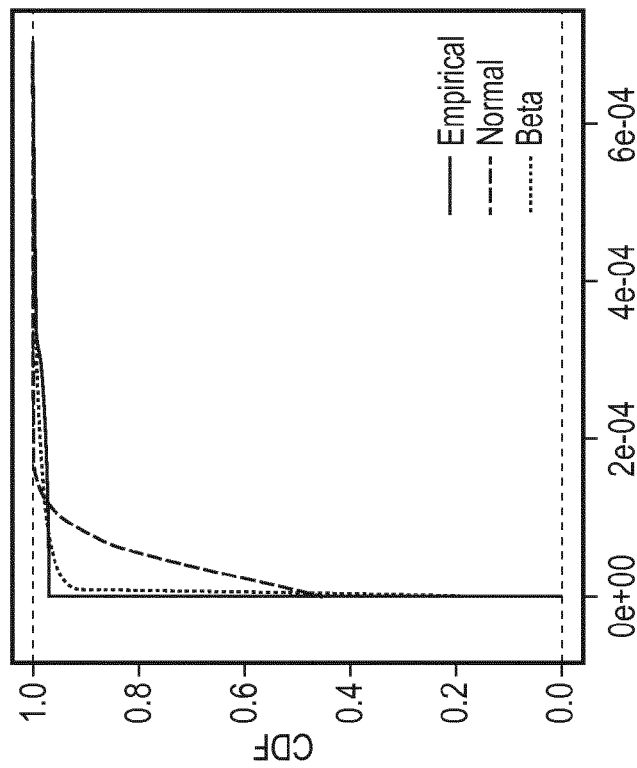
Figure 2C:
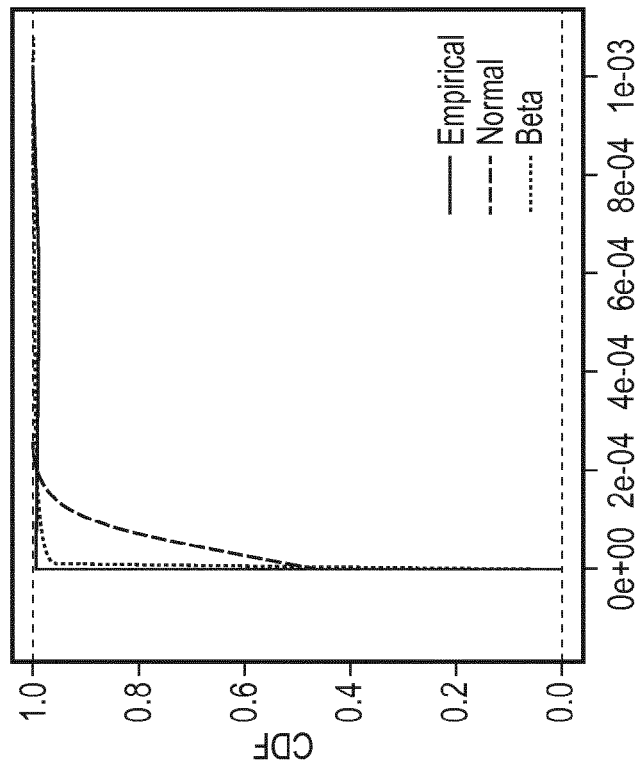
Figure 2D:
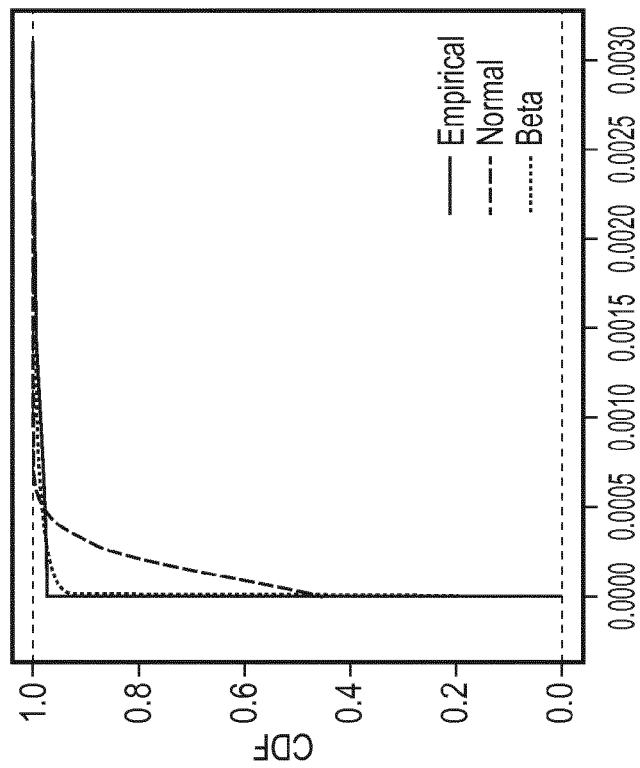

FIG. 1A shows the number of occurrences of different values of the mean AF, binned by increasing values of the AF. The vertical line indicates mean=0.00022, which is at the 95% percentile of the distribution.

FIG. 1B shows the number of occurrences of different values of CV, binned by increasing values of CV. A vertical line indicates CV=18.16, which is at the 95% percentile of the distribution.

Example 2

Determining the AF Required for a Positive Call for a Base Change in a Given Reaction A reaction was defined as positive for a given sequence change if the observed AF was found to be greater than the minimal detectable frequency (MDF) for that allele. The MDF for an allele was calculated as the AF at which the cumulative distribution function (CDF) for that particular base change crosses a predefined threshold (CDF_thresh).

FIG. 2 shows cumulative distributions for several base changes of the panel of Example 1. Cumulative distribution functions for the Normal and Beta distributions are shown, fitted using the values for the mean AF and CV that were calculated for those base changes, compared against the empirical distributions of the data. The Kolmogorov-Smirnov value for goodness of fit for the Normal (KS Normal) and Beta (KS Beta) distributions to the empirical distributions of the data are as follows:

| Base change | KS Normal | KS Beta |
|---|---|---|
| EGFR_D0016_006_R 55248959 C > G | 8.55 | 0.78 |
| EGFR_D0016_009_F 55249159 G > T | 9.26 | 2.89 |
| EGFR_D0016_003_R 55241757 C > A | 9.45 | 0.96 |
| EGFR_D0016_012_R 55259573 G > C | 8.83 | 0.45 |

The process described was used to scan 13,278 possible single-base changes in multiple samples. To maintain a low rate of false-positives, mutations were called if present at an AF such that AF>MDF with a CDF_thresh=0.9999.

The background noise was modelled as a Beta distribution, and for each of the 13,278 possible base changes, given the mean AF and CV measured for the base change in the control samples (FIG. 1), MDF(CDF_thresh) was calculated, which is the AF at which $$F(AF | Mean, CV) = CDF\_thresh$$

where "F" is the CDF of a Beta distribution.

Figure 3B:
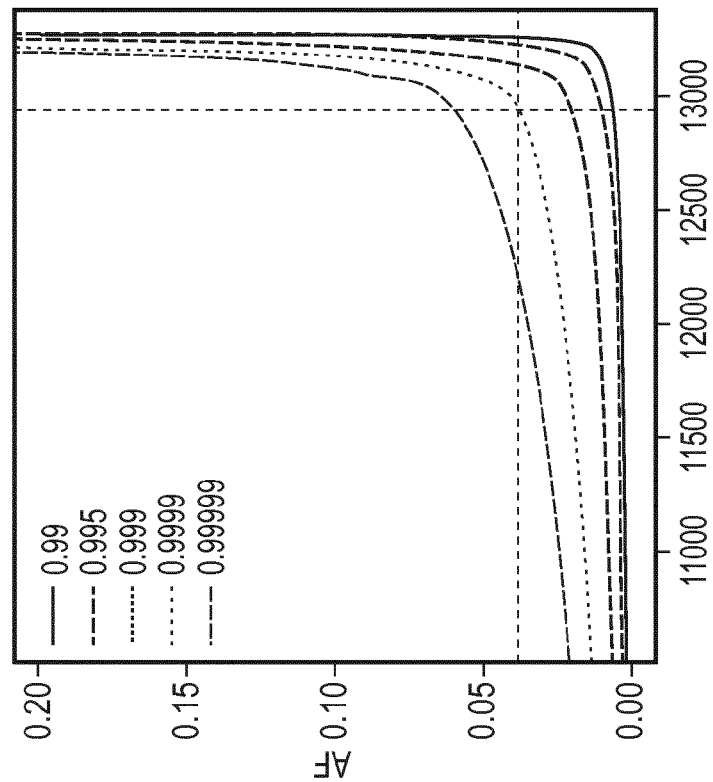
FIG. 3. Graphs showing cumulative values of the Minimal Detectable Frequencies (MDFs) for different values of CDF_thresh. (B) Zoom in of (A). The vertical line indicates the 97.5 percentile point, for which 97.5% of the possible base changes have lower MDF values. For CDF_thresh=0.9999, the 97.5 percentile is at allele frequency (AF)=0.0382, indicated by a horizontal line.
Figure 3A:
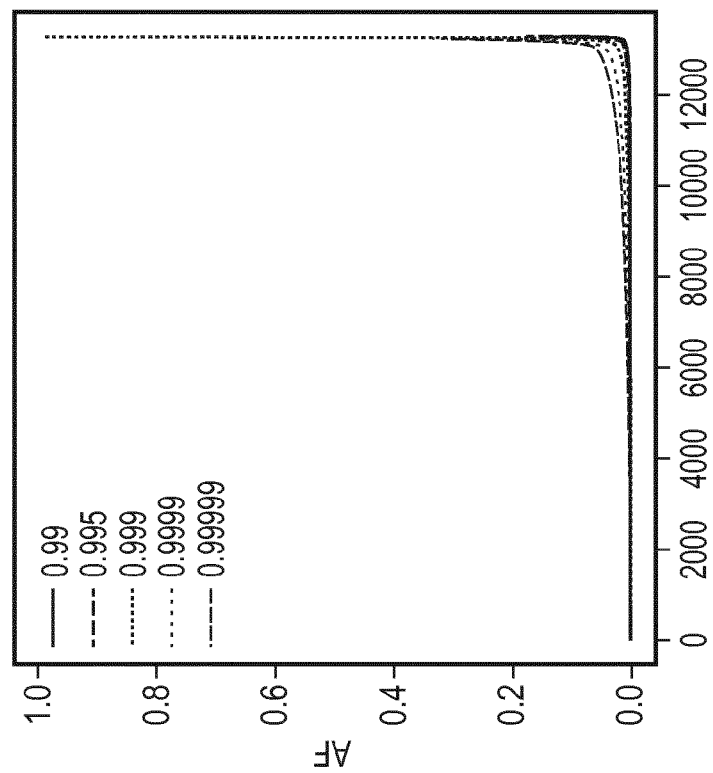

FIG. 3 shows MDF(CDF_thresh) for different values of CDF_thresh (as indicated in the legend). The data in each case is sorted by the values of MDF obtained.

FIG. 3B shows a zoom in. The vertical line indicates the 97.5 percentile point, for which 97.5% of the possible base changes have a lower AF value. For CDF_thresh=0.9999, the 97.5 percentile is at AF=0.0382, indicated by a horizontal line.

Thus it was determined that for the 13,278 possible single-base changes, an MDF at CDF_thresh=0.9999 would be 0.0382 or lower for 97.5% of the possible single base changes (see FIG. 3).

The probability of a false positive determination for a given base change in each reaction (P_fp1), according to this model, is one minus CDF_thresh, which is the value of the CDF at AF=MDF:

$$P\_fp1T = 1 - F(AF = MDF | Mean, CV) = 1 - CDF\_thresh$$

Example 3

Determining the Number of Replicate Amplification Reactions to be Positive for a Given Base Change to Determine Presence of the Base Change in a Sample To minimise false positive determinations for the presence of a base change in a sample, multiple positive replicate amplification reactions (N) were required out of the total number of replicate amplification reactions for that sample (T).

The theoretical probability of a false positive appearing in N out of T reactions (P_fpNT) is $$P\_fpNT = (P\_fp1T)^N * C\_NT = ((1 - CDF\_thresh)^N) * C\_NT$$

where "C_NT" is the number of possibilities of choosing N wells out of T without attention to order, and is $$C\_NT = T! / ((T - N)! * N!)$$

where "!" indicates the factorial function.

For example, for choosing 3 reactions out of 48 there are 17,296 possibilities. For choosing 2 reactions out of 48 there are 1,128 possibilities. The expected rate of false positives was calculated for each sample and is shown in Tables 2 and 3 (FIG. 4).

The requirement to observe multiple positive reactions also increases probability of false negatives, and decreases the probability that a true positive will be observed in multiple reactions.

FIG. 5 shows the Poisson probability of finding at least N number of molecules in the sample as a function of the expected number of molecules (based on the concentration and starting amount of material). The different lines show a different N such that a compound call is made with positive reactions.

The system was designed so that
(i) the total number of replicate amplification reactions (T) for each sample would be much larger than N (here, T≥48), and
(ii) the probability of a call in any reaction would be close to 1 if a mutant molecule was present.

Example 4

Determining the Number of Amplifiable Molecules to be Present in Each Amplification Reaction For an intended dilution rate and the corresponding average number of molecules per reaction, the actual reactions are expected to have a random number of molecules that can be modelled with a Poisson distribution.

A single mutant molecule within each such pool would lead to an observed AF equal to the reciprocal of the number of molecules (assuming that the read fractions are representative of the mutant allele frequency, see Forshew et al. 2012 Sci Transl Med 4(136) 136ra68, FIG. 3B).

Figure 8:
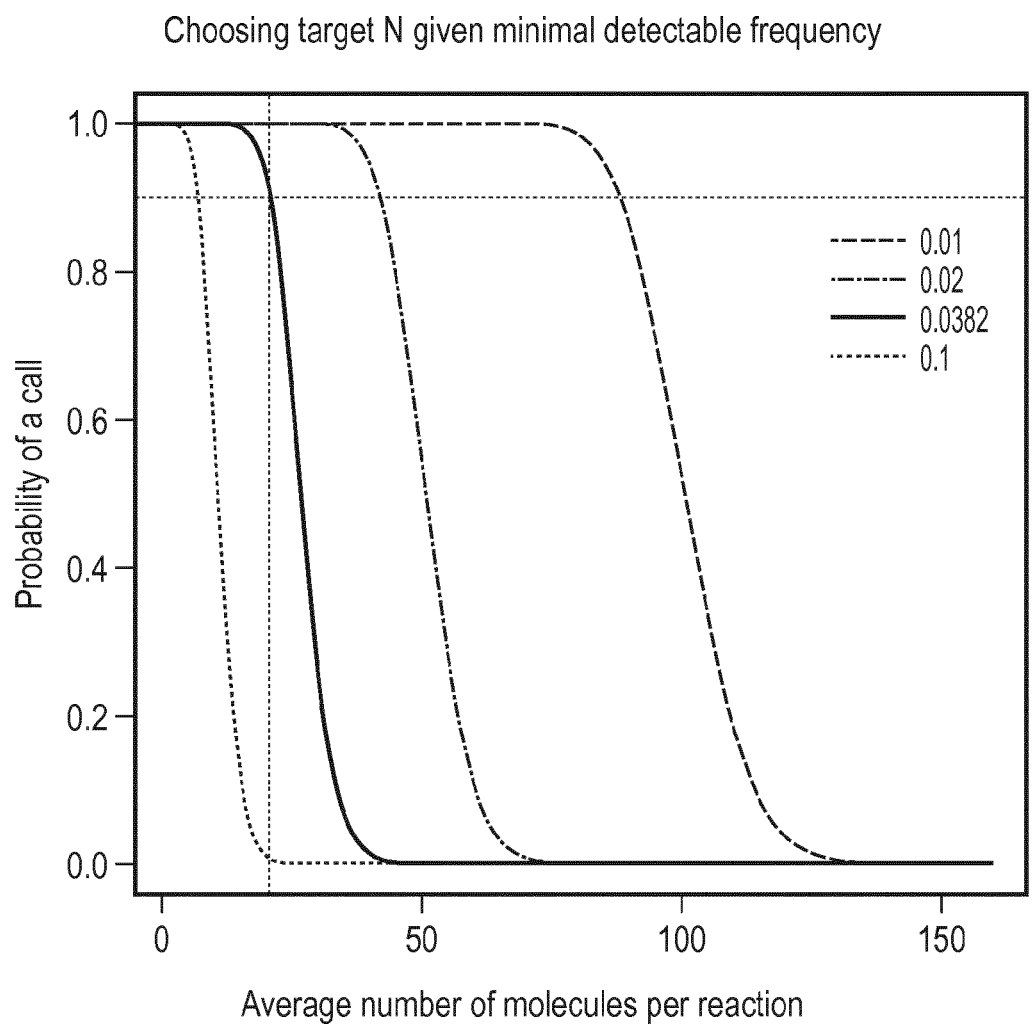
FIG. 8. Graph showing the relationship between the probability of a call and the mean number of molecules per reaction. For different values of a MDF (as indicated in the figure legend), the probability of AF>MDF is plotted as a function of the average number of molecules per reaction based on the template dilution. The horizontal line shows probability=0.90. For MDF=0.0382, a probability of 0.90 that AF>MDF is obtained at an extrapolated N=20.59 (indicated by the vertical line).

For different values of a MDF (as indicated in the figure legend), the probability of AF>MDF was plotted as a function of the average number of molecules per reaction, based on the template dilution (FIG. 8).

The horizontal line shows probability=0.90. For MDF=0.0382 (for which 97.5% of the base changes would pass a CDF_thresh=0.9999, see FIG. 3), a probability of 0.90 that AF>MDF is obtained at an extrapolated N=20.59 (indicated by the vertical line).

A dilution rate for the DNA sample was selected so that each amplification reaction would have an expected 20 amplifiable template molecules, such that for each reaction which has an amplifiable mutant molecule present the probability to have a mutant AF>0.0382 would be >0.9.

The Poisson probability of observing molecules in the samples was approximately equal to the probability of a compound call based on identification of the mutant sequence above the background rates in ≥N reactions. The approximate probability of a false negative is calculated for each sample and is shown in Tables 2 and 3 (FIG. 4).

Example 5

PCR Primers and Design for Proof of Principle Experiments 41 pairs of primers were designed for the panel of 41 amplicons. Each primer was produced with a tagging sequence at the 5' end and one of 7 different barcode sequences in the middle (FIG. 6). The target specific primers were split into two optimised multiplex PCR pools, and the forward and reverse primers were pooled in such a way as to produce 49 different barcode combinations (FIG. 7)

48 of the primer pools were dispensed into different PCR wells using the Fluidigm platform, to do this in high throughput.

DNA was digitally quantified and added so that an average of 20 molecules would enter each PCR. The Fluidigm Access Array has a 68.32% dead volume which was accounted for when adding the DNA (dead vol=33nl*48/5 μl).

This allowed amplification of 48 separate pools of ~20 molecules per sample. For samples where a low frequency alleles was expected, multiple sets of 48 wells were run.

Following the harvest of this first PCR, a second round of PCR was then performed to attach sequencer adapters and sample barcodes.

Libraries were then cleaned and sequenced on both the Illumina MiSeq and HiSeq 2000 sequencers.

Example 6

Proof of Principle in a Dilution Series of Cell Lines

A cell line DNA serial dilution was created where heterozygous mutations were expected to be present at an AF between 3-0.04%. NCI-H1975 and VCAP cell lines have 5 known mutations/SNPs detectable using the primer/amplicon panel described in Example 5 and not present in the LNCaP cell line (Table 4). VCAP, NCI-H1975 and LNCaP DNA were digitally quantified and normalised, and then serially diluted into LNCaP DNA.

TABLE 5

| Cell line | Gene | cDNA change | Protein change | Genomic change (hg19) |
|---|---|---|---|---|
| NCI-H1975 | EGFR | c.2369C > T | p.T790M | chr7: 55249071 C > T |
| NCI-H1975 | EGFR | c.2573T > G | p.L858R | chr7: 55259515 T > G |
| NCI-H1975 | TP53 | c.818G > A | p.R273H | chr17: 7577120 C > T |
| NCI-H1975 | TP53 | SNP | rs17880604 | chr17: 7577644C > G |
| VCAP | TP53 | p.R248W | c.742C > T | chr17: 7577539 G > A |

The method was performed on a dilution series of two cell lines, on a total of 5 different samples, using different numbers of reactions for different samples (see Tables 2 and 3 (FIG. 4)).

The two cell lines differed from LNCaP by 5 single-base polymorphisms in the regions of the genome covered, for a total of 25 positives (50 when calling forward and reverse independently).

To model the background rates, the mean AF and CV at each position in the region of interest were used to estimate parameters and fit a Beta distribution specific for each locus and each possible base change.

Based on the model above and calculations in Tables 2 and 3 (FIG. 4), using CDF_thresh=0.9999 and a compound call requiring multiple (N) positive reactions, the following results were obtained.

$N \geq 2$

Overall sensitivity of 0.96, 36 false positive compound calls. Table 2 (FIG. 4A) shows sensitivity at different dilution rates.

$N \geq 3$

Overall sensitivity of 0.90, 1 false positive compound call. Table 3 (FIG. 4B) shows sensitivity at different dilution rates.

Figure 9B:
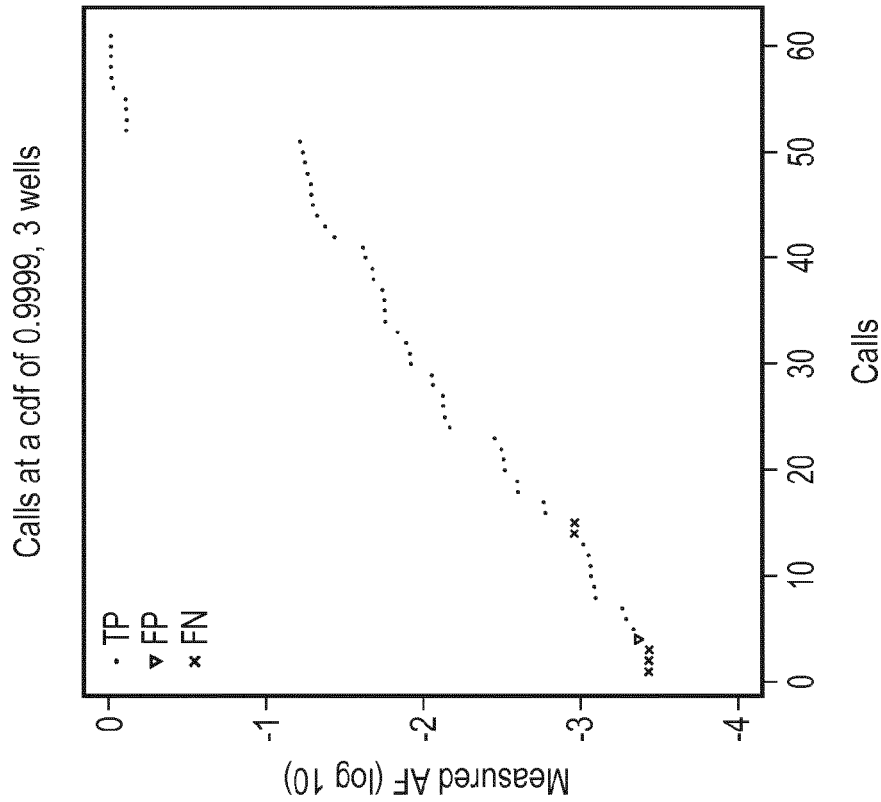
FIG. 9. Plots showing Mutations identified (true positives (TP)), false positive calls (FP), and mutations missed (false negatives (FN)) by performing the method on a dilution series of DNA from three cell lines. (A) CDF cut-off=0.9999 on a Beta distribution with N≥2. (B) CDF cut-off=0.9999 on a Beta distribution with N≥3.
Figure 9A:
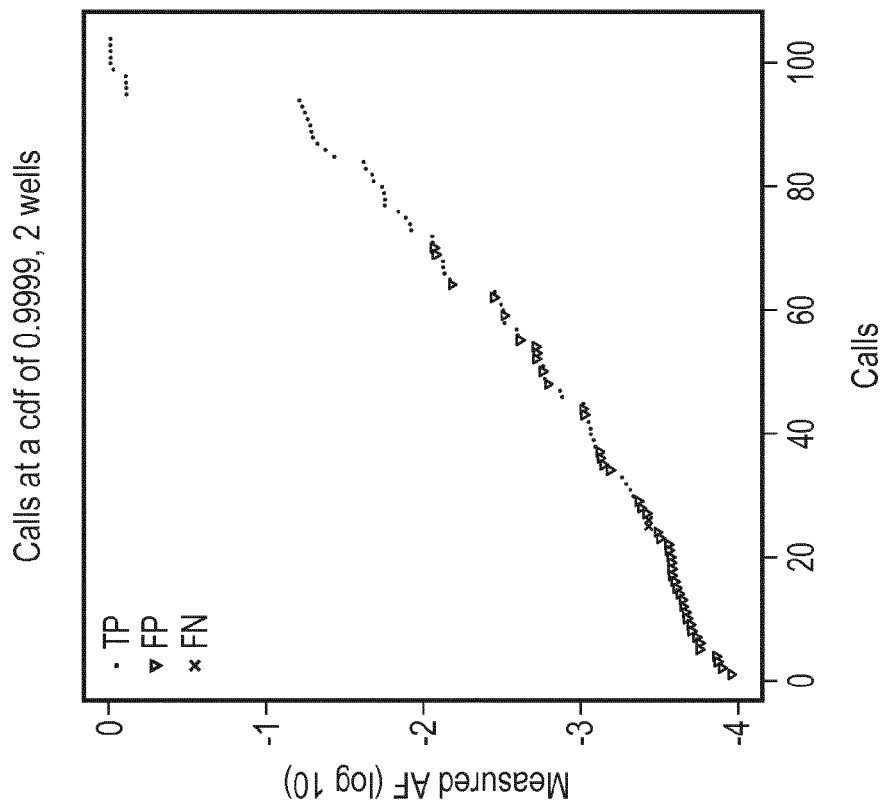

Mutations identified (true positives (TP)), false positive calls (FP), and mutations missed (false negatives (FN)) by performing the method on a dilution series of DNA from two cell lines are shown in Table 4 and FIG. 9. Data points in FIG. 9 are ordered by increasing measured AF, showing for each mutation the measured AF, except for FN mutations, which show the expected AF.

Figure 10:
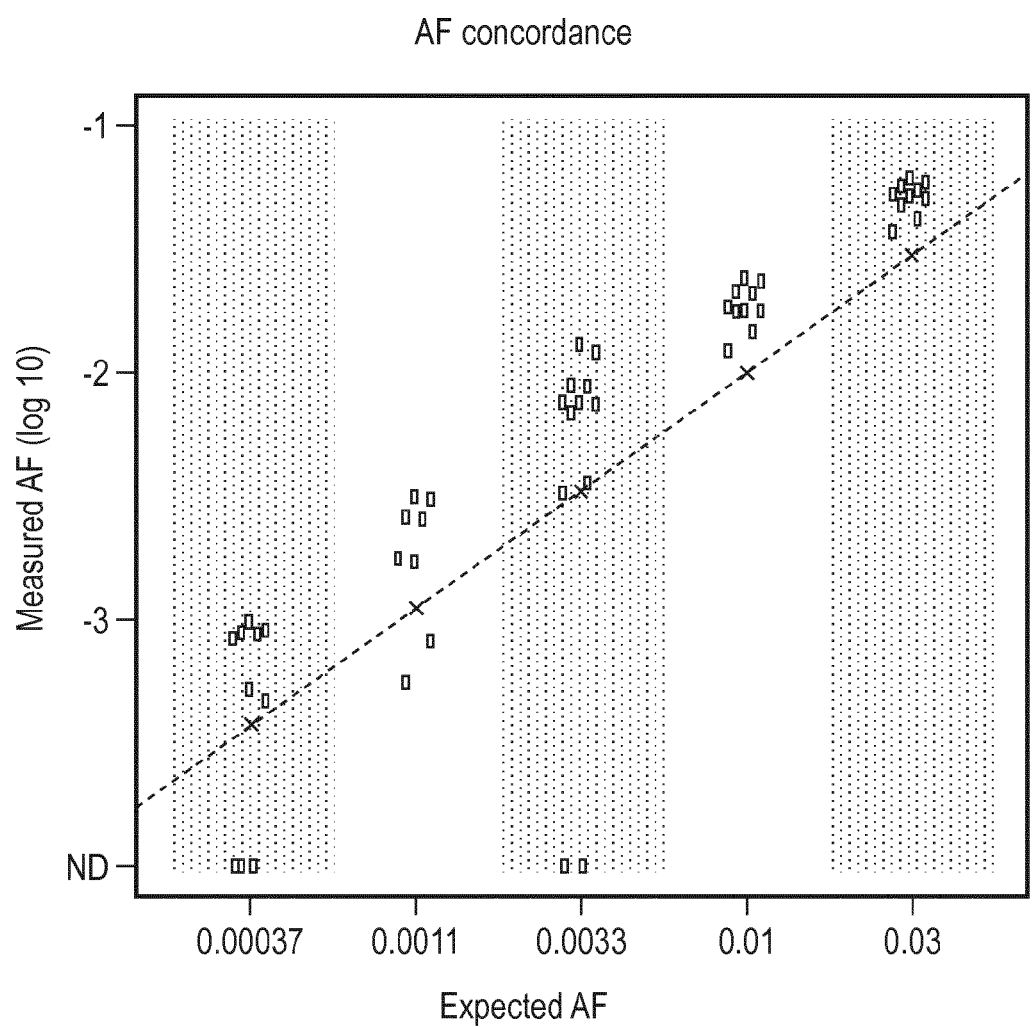
FIG. 10. Plot showing concordance between expected and measured AF. False negatives are shown as "Not Detected" (ND) on the vertical axis. Expected values are shown as crosses, connected by a dotted line as a guide to the eye.

FIG. 10 shows concordance between expected and measured AF Based on compound mutation calls using CDF_thresh=0.9999 and N≥3. False negatives are shown as "Not Detected" (ND) on the vertical axis. Expected values are shown as crosses, connected by a dotted line as a guide to the eye.

Example 7

Proof of Principle with Alternative Method of Mutation Calling

The method was performed on a dilution series as described in Example 6.

VCAP and NCI-H1975 DNA was diluted serially into LNCaP DNA as shown in Table 6.

TABLE 6

| Name | % mutant | Mutant mols per reaction | Repeats | Total Mut mols |
|---|---|---|---|---|
| DIL 3% | 3 | 28.8 | 1 × 48 = 48 | 28.8 |
| DIL 1% | 1 | 9.6 | 2 × 48 = 96 | 19.2 |
| DIL 0.33% | 0.33 | 3.20 | 2 × 48 = 96 | 6.4 |
| DIL 0.11% | 0.11 | 1.07 | 6 × 48 = 288 | 6.4 |
| DIL 0.037% | 0.04 | 0.36 | 12 × 48 = 576 | 4.266667 |

In the first experiment 7(×48) LNCaP, 1(×48) VCAP, 1(×48) NCI-H1975 then 1 or more of the dilutions were sequenced (Table 6, "Repeats").

Mutation Calling

336 LNCaP PCR reactions were used to determine the background AF at each base. A Normal distribution was used to model background for all possible bases from the non-reference base at all positions of the region of interest.

Each reaction was then screened for changes at each base differing from the background by a specified z-score and depth. Base changes identified a specified number of times above this score were determined to have the mutation.

Results

Mutation calling was first performed using a z-score cut-off of 20 and 3 positive wells. Table 7 shows mutation detection results.

All mutations/SNPs were detected down to 0.33%. Of an estimated 1,920 molecules screened in the 0.33% dilution (2 samples×48 wells×20 DNA molecules), between 4 and 12 positive wells/molecules were detected, corresponding to almost exactly to 0.33% (Table 7, Dil 0.33).

In the 0.11% dilution 4 of the 5 changes were detected. 1 was missed as only 2 wells were positive (Table 7, Dil 0.11).

Finally in the 0.037% dilution 1 of 5 mutations was missed entirely; another (chr17: 7577644 C>G) was missed in one of the two overlapping amplicons. These results fit with the random distribution of these mutant molecules (Table 7, Dil 0.037).

The 2 false positive reactions were most likely due to polymerase error during early rounds of library amplification. Such errors should typically be at lower frequencies than normal changes.

By increasing our z-score cut-off to 30 all real changes were kept, and the 2 false positives were removed (Table 7).

TABLE 7 number of positive reactions determined by z-score greater than 30. For true positives, this number is averaged over the two overlapping amplicaons (forward and reverse). False positive calls are shown if at least the minimum of 3 reactions was positive.

| Expected changes | NCI-H1975 | VCAP | DIL 3 | DIL 1 | DIL 0.33 | DIL 0.11 | DIL 0.037 |
|---|---|---|---|---|---|---|---|
| chr17: 7577120 C > T | 48 | 0 | 26 | 27.5 | 4 | 6.5 | 3 |
| chr17: 7577539 G > A | 0 | 48 | 19.5 | 18 | 5.5 | 2 | 0 |
| chr17: 7577644 C > G | 46.5 | 0 | 29 | 22 | 11.5 | 3 | 2.5 |
| chr7: 55249071 C > T | 47.5 | 0 | 21.5 | 15 | 6.5 | 8 | 4 |
| chr7: 55259515 T > G | 41 | 0 | 17 | 9.5 | 8 | 7 | 3 |
| False positives |   |   |   |   |   |   |   |
| chr17: 7576861 T > C | 0 | 0 | 0 | 0 | 0 | 2* | 0 |

*called at z-score = 20

The invention claimed is:

1. A method for detecting a genetic variant in a region of interest in a DNA sample comprising
   (i) determining, for a given sequencing platform, sequencing process and sequencing depth, the distribution of the number of reads supporting a genetic variant or plurality of genetic variants expected to be observed in the sequencing results of amplification reactions due to amplification and sequencing error (read count distribution);
   (ii) based on the read count distribution determined in step (i), establishing a threshold frequency at or above which each genetic variant must be observed in sequencing results of amplification reactions to assign a positive determination for the presence of the genetic variant in a given amplification reaction;
   (iii) partitioning the DNA sample into a plurality of replicate amplification reactions, so that the mean number of amplifiable template molecules of the region of interest in a replicate amplification reaction is fewer than the reciprocal of the threshold frequency determined in step (ii);
   (iv) performing the amplification reactions of step (iii) and sequencing the products of amplification reactions,
   (v) based on step (ii) and the results of step (iv), determining the presence/absence of the genetic variant in each replicate amplification reaction; and
   (vi) integrating the results of (v) to determine the presence/absence of the genetic variant in the region of interest in the DNA sample.

2. The method according to claim 1, wherein for the genetic variant to be determined as being present in the region of interest in the DNA sample in step (vi), a positive determination for the presence of the genetic variant must be made in more than one replicate amplification reaction in step (v).

3. The method according to claim 2, wherein for the genetic variant to be determined as being present in the region of interest in the DNA sample in step (vi), a positive determination for the presence of the genetic variant must be made in at least 3 replicate amplification reactions in step (v).

4. The method according to claim 1, wherein the threshold frequency of step (ii) is the frequency at which the cumulative distribution function value for the probability of observing the genetic variant at that frequency is 0.99 or greater.

5. The method according to claim 1, wherein threshold frequency of step (ii) is determined using a binomial, over-dispersed binomial, Beta, Normal, Exponential or Gamma probability distribution model.

6. The method according to claim 1, wherein the threshold frequency of step (ii) is the frequency where the z-score is 20.

7. The method according to claim 1, wherein establishing a threshold frequency at or above which the genetic variant must be observed in sequencing results of amplification reactions to assign a positive determination for the presence of the genetic variant in a given amplification reaction comprises
   (a) based on the read count distribution determined for a plurality of genetic variants in step (i), establishing a plurality of threshold frequencies at or above which the genetic variants should be observed in sequencing results of amplification reactions to assign a positive determination for the presence of the genetic variant in a given amplification reaction, and
   (b) based on step (a), establishing an overall threshold frequency at or above which a genetic variant must be observed in sequencing results of a given amplification reaction to assign a positive determination for the presence of the genetic variant in that amplification reaction, which is the threshold frequency at which at least 90% of the plurality of threshold frequencies determined in step (a) are less than this value.

8. The method according to claim 1, wherein the mean number of amplifiable template molecules to be present in a replicate amplification reaction is the number at which when the genetic variant is present in a single amplifiable template molecule of a replicate amplification reaction, the probability that a positive determination will be made for that replicate is 0.9 or greater.

9. The method according to claim 1, wherein step (i) comprises sequencing a DNA sample multiple times to determine the read count distribution for a genetic variant or plurality of genetic variants.

10. The method according to claim 1, wherein the read count distribution at which a genetic variant or plurality of genetic variants is expected to be observed in the sequencing results of amplification reactions due to amplification and sequencing error is determined in step (i) based on sequencer and/or polymerase error rates, optionally taking sequence context into account.

11. The method according to claim 1, wherein following partitioning of the DNA sample in step (iii), each replicate amplification reaction has more than a single amplifiable template molecule for the region of interest per replicate amplification reaction.

12. The method according to claim 11, wherein the mean number of amplifiable template molecules per replicate amplification reaction is more than 1 and less than 1000.

13. The method according to claim 1, wherein partitioning the DNA sample into a plurality of replicate amplification reactions comprises diluting the DNA sample and aliquoting into replicate amplification reactions.

14. The method according to claim 1, wherein replicate amplification reactions are performed in parallel, and sequencing of the products of amplification reactions is performed in parallel.

15. The method according to claim 1, wherein amplification reactions are performed using one or more primers flanking the region of interest and which integrate sample and/or amplification reaction replicate specific identifier sequences into the products of amplification and/or wherein the primers integrate sequence adapters into the products of amplification.

16. The method according to claim 1, wherein a plurality of regions of interest are analysed in parallel.

17. The method according to claim 1, wherein the method further comprises:
(vii) determining the frequency of the genetic variant in the DNA sample.

18. The method according to claim 1, wherein the read count distribution is defined as a normal distribution characterised by parameters which are the mean frequency and variance of the frequency at which a genetic variant or plurality of genetic variants is observed or expected to be observed in the sequencing results of amplification reactions due to amplification and sequencing error.

19. A method for detecting and/or quantifying a genetic variant in a sample of cell-free DNA obtained from a cancer patient, the method comprising:
(i) determining, for a given sequencing platform, sequencing process and sequencing depth, the distribution of the number of reads supporting a genetic variant or plurality of such genetic variants expected to be observed in the sequencing results of amplification reactions due to amplification and sequencing error (read count distribution);
(ii) based on the read count distribution determined in step (i), establishing a threshold frequency at or above which the genetic variant must be observed in sequencing results of amplification reactions to assign a positive determination for the presence of the genetic variant in a given amplification reaction;
(iii) partitioning the DNA sample obtained from a subject into a plurality of replicate amplification reactions, so that the mean number of amplifiable template molecules of the region of interest in a replicate amplification reaction is fewer than the reciprocal of the threshold frequency determined in step (ii);
(iv) performing the amplification reactions of step (iii) and sequencing the products of amplification reactions,
(v) based on step (ii) and the results of step (iv), determining the presence/absence of a genetic variant in each replicate amplification reaction,
(vi) integrating the results of (v) to detect the presence of the genetic variant in the region of interest in the DNA sample, thereby detecting and/or quantifying the genetic variant in the sample of cell-free DNA from the cancer patient.

20. A method for diagnosis or prognosis or monitoring a disease, for selecting a patient for a therapy or identifying genetic variation predictive of susceptibility, or for evaluating response or resistance to a therapy, said method comprising carrying out the method of claim 1 on a DNA sample obtained from a subject who has or is suspected of having a disease or who is undergoing therapy to treat a disease.

* * * * *